United States Patent
Ashton et al.

(10) Patent No.: US 6,478,785 B1
(45) Date of Patent: Nov. 12, 2002

(54) DISPOSABLE PANT-TYPE DIAPER HAVING ENHANCED EXTENSIBILITY AROUND WAIST OPENING

(75) Inventors: Gregory Ashton, Kobe (JP); Eiro Fukuda, Akashi (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/700,563

(22) PCT Filed: May 28, 1998

(86) PCT No.: PCT/US98/10849
§ 371 (c)(1),
(2), (4) Date: Nov. 16, 2000

(87) PCT Pub. No.: WO99/60969
PCT Pub. Date: Dec. 2, 1999

(51) Int. Cl.[7] .................................................. A61F 13/15
(52) U.S. Cl. ............................ 604/385.01; 604/385.24; 604/392
(58) Field of Search ................................. 604/317–402; 2/400–408, 227

(56) References Cited

U.S. PATENT DOCUMENTS

| 4,743,241 | A | | 5/1988 | Igaue et al. |
| 5,370,634 | A | * | 12/1994 | Ando et al. ............... 604/385.1 |
| 5,383,871 | A | | 1/1995 | Carlin et al. |
| 5,591,155 | A | | 1/1997 | Nishikawa et al. |
| 5,685,874 | A | * | 11/1997 | Beull et al. ................. 604/396 |
| 5,897,545 | A | | 4/1999 | Kline et al. |

FOREIGN PATENT DOCUMENTS

| WO | WO 93/24085 | 12/1993 |
| WO | WO 94/28841 | 12/1994 |
| WO | WO 97/36566 | 10/1997 |

* cited by examiner

Primary Examiner—Jeanette Chapman
(74) Attorney, Agent, or Firm—Michael P. Hayden; David W. Weirich; Ken K. Patel

(57) ABSTRACT

A disposable garment having enhanced extensibility around waist opening is disclosed. The disposable garment has a front region, a back region and a crotch region between the front region and the back region. The disposable garment comprises a chassis and seams. The chassis comprises a topsheet, a backsheet joined with the topsheet, and an absorbent core interposed between the topsheet and the backsheet. The chassis has a central panel having side edges and a waist edge, and an ear panel extending laterally outwardly from each side edge of the central panel in the front region and the back region. The ear panel is rendered extensible to form an extensible ear. The extensible ear has a higher end edge, a lower end edge, an inner side edge, and an outer side edge. The outer side edge is non-parallel to the inner side edge, and is non-parallel to a longitudinal center line of the garment, and projects laterally outwardly proximate the higher end edge. A lateral width of the extensible ear between the inner side edge and the outer side edge is greater proximate the higher end edge than proximate the lower end edge. The seams join each ear panel along the outer side edge to a corresponding portion in the opposite region of the disposable garment so as to form one waist opening and two leg openings. The seam is non-parallel to the longitudinal canter line.

10 Claims, 19 Drawing Sheets

DISPOSABLE PANT-TYPE DIAPER HAVING ENHANCED EXTENSIBILITY AROUND WAIST OPENING

FIELD

The present invention relates to disposable garments. Examples of such disposable garments include disposable underwear, disposable diapers including pull-on diapers and training pants, and disposable panties for menstrual use. More specifically, the present invention relates to disposable garments having enhanced extensibility around a waist opening.

BACKGROUND

Infants and other incontinent individuals wear disposable garments such as diapers to receive and contain urine and other body exudes. Pull-on garments having fixed sides (e.g., training pants or pull-on diapers) have become popular. In order to contain body exudates as well as to fit a wide variety of body shapes and sizes, these garments must fit snugly about the waist and legs of the wearer without drooping, sagging or sliding down from its position on the torso as well as fitting larger wearers without causing irritation to the skin due to the product being too tight.

Many types of pull-on garments use conventional elastic elements secured in an elastically contractible condition in the waist and leg openings. For example, pull-on garments known as "balloon type" pants are contracted by elasticized bands in specific zones of the product while the remaining material tends to blouse. Examples of such pull-on garments are disclosed in U.S. Pat. No. 5,171,239 published on Dec. 15, 1992, and U.S. Pat. No. 4,610,681 published on Sep. 9, 1986. These garments will fit a range of waist and leg sizes due to the fact that the contractive elastic openings will expand to accommodate various size wearers. Nonetheless, the range of sizes is limited because the elastic elements, which enable this variation in size, have a limited degree of stretch. The narrow elastic bands used in the waist opening and the leg openings also tend to concentrate the fit forces in a narrow zone of the wearer's body leading to increased incidence of skin marking of the wearer.

Another type of pull-on garment employs side panels. Examples of such garments are disclosed in U.S. Pat. No. 4,940,464 published on Jul. 10, 1990, U.S. Pat. No. 5,246,433 published on Sep. 21, 1993, U.S. Pat. No. 5,545,158 published on Aug. 13, 1996, U.S. Pat. No. 5,591,155 published on Jan. 7, 1997, and EP publication 0 526 868 A1 published on Feb. 10, 1993. Such garments have side panels which extend laterally outwardly in a front region of the garments and the back region of the garments. The side panel has an inner side edge and an outer side edge, both of which are parallel to each other and parallel to the longitudinal center line of the garment. The garments also have seams to join the outer side edges of the side panels to form one waist opening and two leg openings. Since the outer side edges are parallel to each other and parallel to the longitudinal center line of the garments, each side elastic incorporated in the side panel has the same width in the lateral direction or the same available elastic material quantity on the side panel between the waist opening and the leg openings. Therefore, these garments do not have a high degree of extensibility around the waist opening, but have only a uniform degree of extensibility between the waist opening and the leg openings. Therefore, if the garment fits the wearer well around the leg openings and provides a sustained fit around the leg openings, the wearer may feel tightness around the waist opening thereby causing an incidence of skin marking of the wearer. In addition, because these garments do not have sufficient extensibility, these garments do not provide wider waist opening for application of the garments to the wearer. This results in difficulty of application of the pull-on diaper.

Thus, none of the existing art provides all of the advantages and benefits of the present invention.

SUMMARY

The present invention is directed to a disposable garment. The disposable garment has a front region, a back region and a crotch region between the front region and the back region. The disposable garment comprises a chassis and seams. The chassis comprises a topsheet, a backsheet joined with the topsheet, and an absorbent core interposed between the topsheet and the backsheet. The chassis has a central panel having side edges and a waist edge, and an ear panel extending laterally outwardly from each side edge of the central panel in the front region and the back region. The ear panel is rendered extensible to form an extensible ear. The extensible ear has a higher end edge, a lower end edge, an inner side edge, and an outer side edge. The outer side edge is non-parallel to the inner side edge, and is non-parallel to a longitudinal center line of the garment, and projects laterally outwardly proximate the higher end edge. A lateral width of the extensible ear between the inner side edge and the outer side edge is greater proximate the higher end edge than proximate the lower end edge. The seams join each ear panel along the outer side edge to a corresponding portion in the opposite region of the disposable garment so as to form one waist opening and two leg openings. The seam is non-parallel to the longitudinal canter line.

These and other features, aspects, and advantages of the present invention will become evident to those skilled in the art from a reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying drawings and which like designations are used to designate substantially identical elements, and in which:

DETAILED DESCRIPTION

All cited references are incorporated herein by reference in their entireties. Citation of any reference is not an admission regarding any determination as to its availability as prior art to the claimed invention.

Herein, "pull-on garment" refers to articles of wear which have a defined waist opening and a pair of leg openings and which are pulled onto the body of the wearer by inserting the legs into the leg openings and pulling the article up over the waist. Herein "disposable" is used to describe garments which are not intended to be laundered or otherwise restored or reused as a garment (i.e., they are intended to be discarded after a single use and, preferably, to be recycled, composted or otherwise disposed of in an environmentally compatible manner). A "unitary" pull-on garment refers to pull-on garments which are formed of separate parts united together to form a coordinated entity, but the ear panels are not separate elements joined to a separate chassis in that the ear panels are formed by at least one layer which also forms the central panel or chassis of the garment (i.e., the garment does not require separately manipulative panels such as a separate chassis and separate ear panels). The pull-on garment is also preferably "absorbent" to absorb and contain the various exudates discharged from the body. A preferred embodiment of the pull-on garment of the present invention is the unitary disposable absorbent pull-on garment, pull-on diaper 20, shown in FIG. 1. Herein, "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like. Herein "joined" or "joining" encompasses configurations whereby an element is directly secured to the other element by affixing the element directly to another element, and configurations whereby the element is indirectly secured to the other element by affixing the element to intermediate member(s) which in turn are affixed to the other element.

Figure 1:
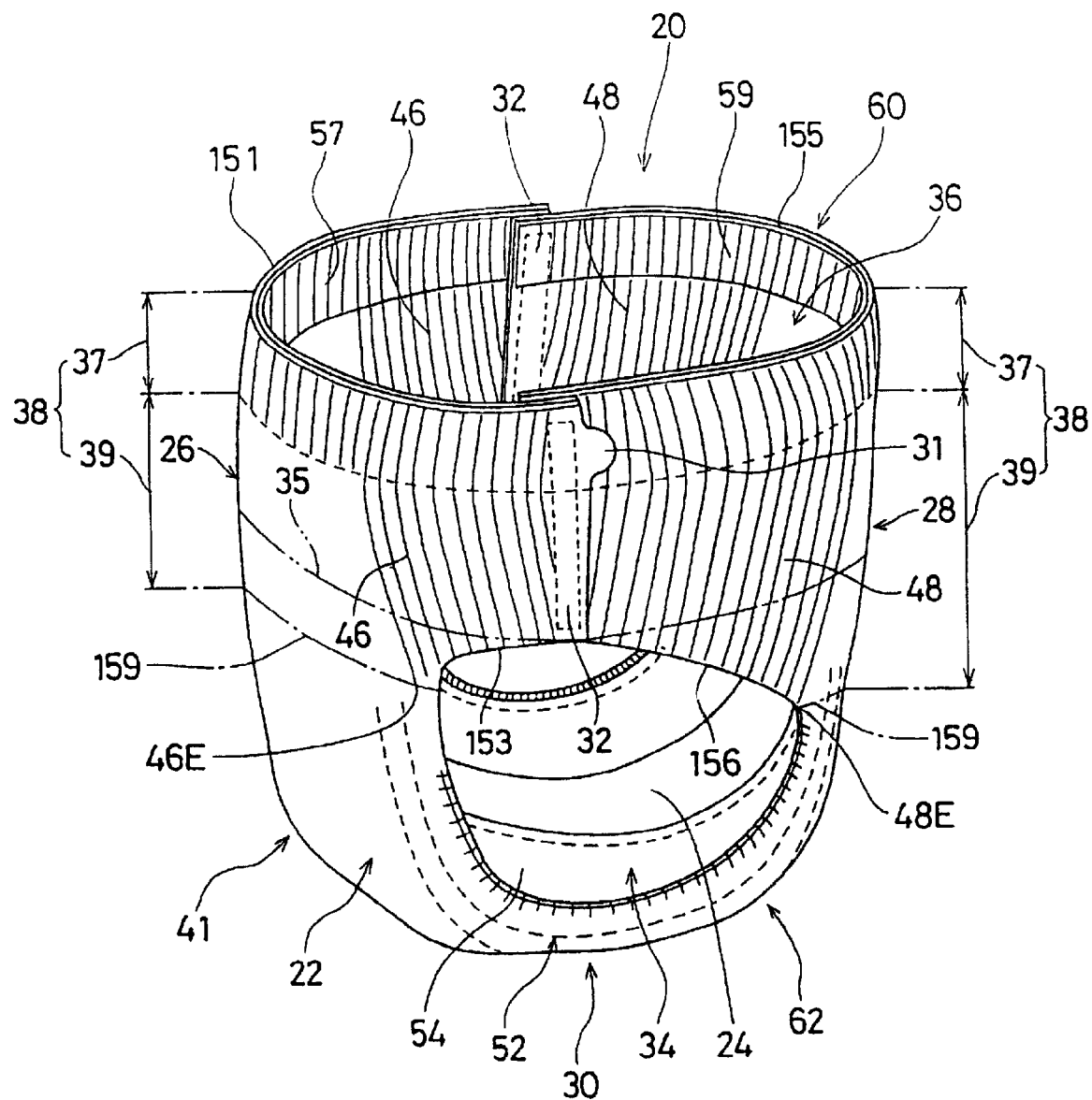
FIG. 1 is a perspective view of a preferred embodiment of the disposable pull-on garment of the present invention in a typical in use configuration.
Figure 2:
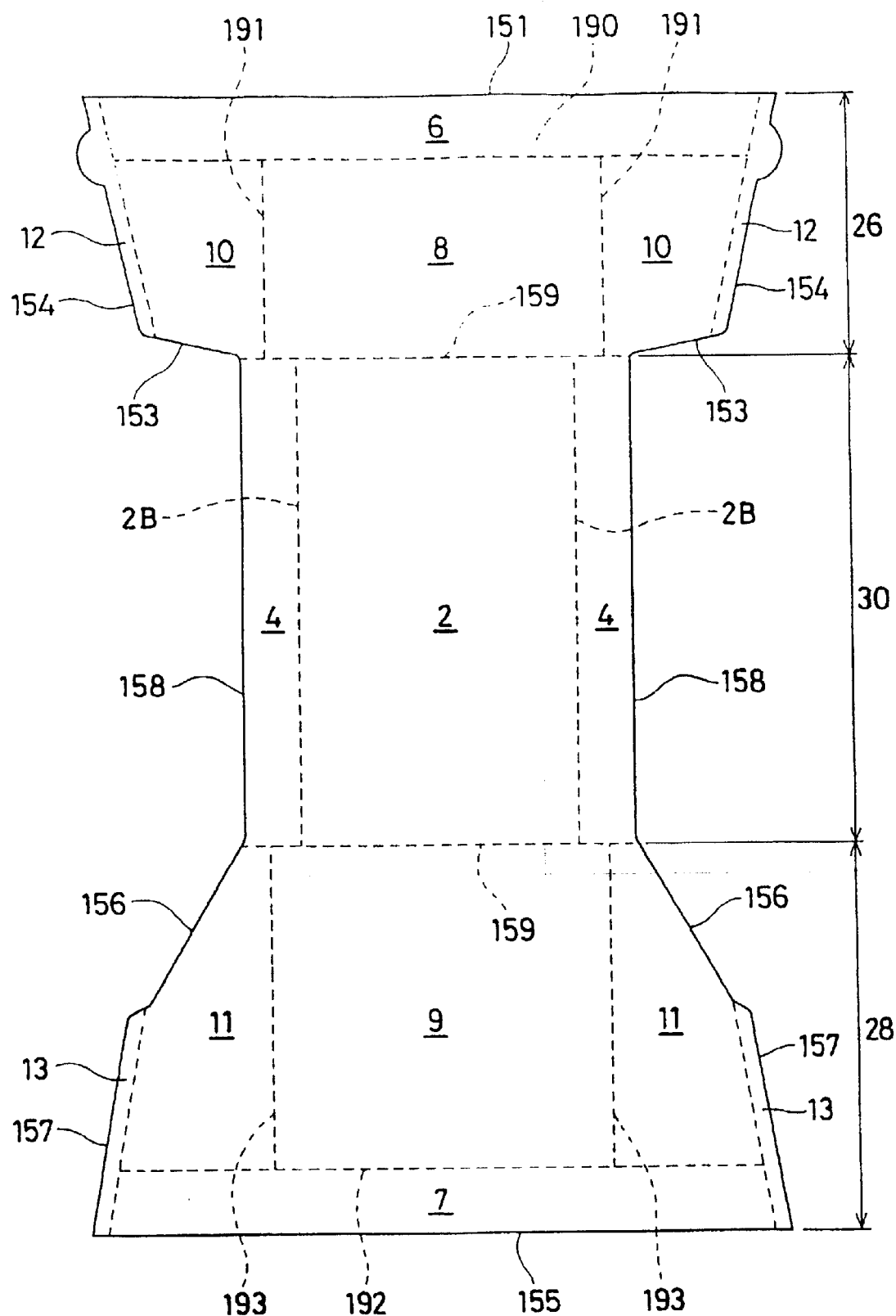
FIG. 2 is a simplified plan view of the disposable pull-on garment of the present invention in its flat uncontracted, unseamed condition showing the various panels of the garment.
Figure 3:
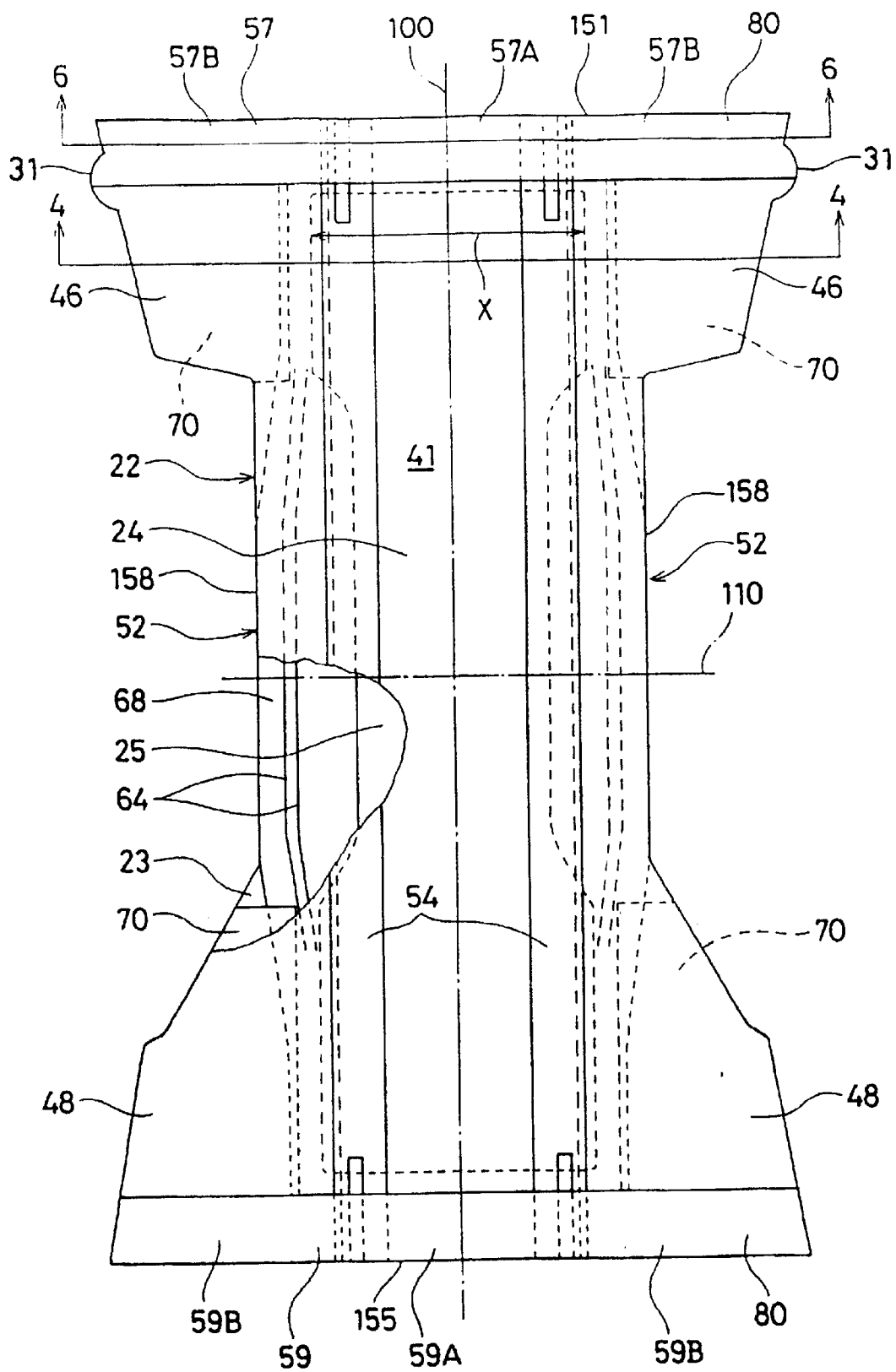
FIG. 3 is a simplified plan view of the embodiment shown in FIG. 1 in its flat uncontracted, unseamed condition.

Referring to FIGS. 1, 2, and 3, the pull-on diaper 20 has the front region 26, the back region 28 and the crotch region 30 between the front region 26 and the back region 28. The pull-on diaper 20 also has two centerlines; a longitudinal centerline 100 and a transverse centerline 110. Herein "longitudinal" refers to a line, axis, or direction in the plane of the pull-on diaper 20 that is generally aligned with (e.g. approximately parallel with) a vertical plane which bisects a standing wearer into left and right halves when the pull-on diaper 20 is worn. Herein "transverse" and "lateral" are interchangeable and refer to a line, axis or direction which lies within the plane of the diaper that is generally perpendicular to the longitudinal direction (which divides the wearer into front and back body halves). The pull-on diaper 20 and component materials thereof also have a body-facing surface which faces the skin of wearer in use and an outer-facing surface which is the opposite surface to the body-facing surface.

FIG. 2 shows a simplified plan view of the pull-on diaper 20 of FIG. 1 in its flat-out, uncontracted state depicting the various panels and their positioning with respect to each other. The term "panel" is used herein to denote an area or element of the pullon diaper or the belt. (While a panel is typically a distinct area or element, a panel may coincide (functionally correspond) somewhat with a adjacent panel.) The pull-on diaper 20 has a crotch region 30 comprising a main panel 2 and a pair of leg flap panels 4; a front region 26 comprising a central panel (medial panel) 8, a waistband panel 6, ear panels 10, and seam panels 12; and a back region 28 comprising a central panel (medial panel) 9, a waistband panel 7, ear panels 11, and seam panels 13. The crotch region 30 is the portion of the pull-on diaper 20 from which the continuous belt (the other panels) emanates. The absorbent core is generally positioned within the main panel 2 since exudates are typically discharged in this region although the absorbent core will typically extend into the medial panels 8 and 9 of the belt. A leg flap panel 4 extends generally laterally outwardly from and along each side edge 2B of the main panel 2. Each leg flap panel 4 generally forms at least a portion of the elastic leg feature. The continuous belt zone (the front region 26 and the back region 28) extends generally longitudinally outwardly from and along each lateral edge 159 of the crotch region 30 (the main panel 2 and the leg flap panel 4). In the front region 26, the medial panel 8 (i.e., central panel) extends generally longitudinally outwardly from and along the lateral edge 159 of the crotch region 30. The medial panel 8 has a waist edge 190 and side edges 191. The ear panels 10 each extend generally laterally outwardly from and along the side edge 191 of the medial panel 8 (i.e., central panel). The ear panel 10 has a waist edge 161 and a side edge 171. The waistband panel 6 extends generally longitudinally outwardly from and along the waist edge 190 of the medial panel 8 (i.e., central panel) and the waist edge 161 of the ear panel 10. The waistband panel 6 has side edges 175. The seam panels 12 each extend generally laterally outwardly from and along the side edge 171 of the ear panel 10 and the side edge 175 of the waistband panel 6. In the back region 28, the medial panel 9 (i.e., central panel) extends generally longitudinally outwardly from and along the other lateral edge 159 of the crotch region 30. The medial panel 9 has a waist edge 192 and side edges 193. The ear panels 11 each extend generally laterally outwardly from and along the side edge 193 of the medial panel 9 (i.e., central panel). The ear panel 11 has a waist edge 163 and a side edge 173. The waistband panel 7 extends generally longitudinally outwardly from and along the waist edge 192 of the medial panel 9 (i.e., central panel) and the waist edge 163 of the ear panel 11. The waistband panel 7 has side edges 177. The seam panels 13 each extend generally laterally outwardly from and along the side edge 173 of the ear panel 11 and the side edge 177 of the waistband panel 7. The front region 26, in addition to its panels, also has a waist edge 151, leg edges 153, and side edges 154. The back region 28, in addition to its panels, also has a waist edge 155, leg edges 156, and side edges 157. The crotch region 30 has leg edges 158.

The pull-on diaper 20 primarily comprises a chassis 41, a waist elastomeric material (not shown in FIGS. 1, 2, and 3), a side elastomeric material (not shown in FIGS. 1, 2, and 3), and seams 32. The pull-on diaper 20 may have tear open tabs 31, whose positioning is associated with the seams 32 and elasticized leg cuffs 52 including inner barrier cuffs 54. The side elastomeric material renders at least a part of the ear panel 10 and 11 extensible, thereby forming extensible ear 46 and 48. The waist elastomeric material renders at least a part of the waistband panel 6 and 7 extensible, thereby forming continuous extensible waistband 57 and 59. The side elastomeric material and the waist elastomeric material are separate elements to each other and disposed so as not to overlap to each other in the longitudinal direction of the pull-on diaper 20. This allows more independent behavior of the waist and side elastomeric materials to allow for adjustments in dimension extension, pressure, etc. The extensible ear 46 and 48 and continuous extensible waistband 57 and 59 are extensible at least in the lateral direction. The seam 32 joins the seam panel 12 in the front region 26 to the seam panel 13 in the back region 28, whereby the ear panel 10 is joined to the ear panel 11 and whereby one waist opening 36 and two leg openings 34 are formed. In the configuration where the ear panel 10 is joined to the ear panel 11, the continuous extensible waistband 57 and 59 forms a continuous extensible waist feature 60 about the waist opening 36. Further, a continuous belt zone 38 extends in the front region 26 and the back region 28.

Figure 4:
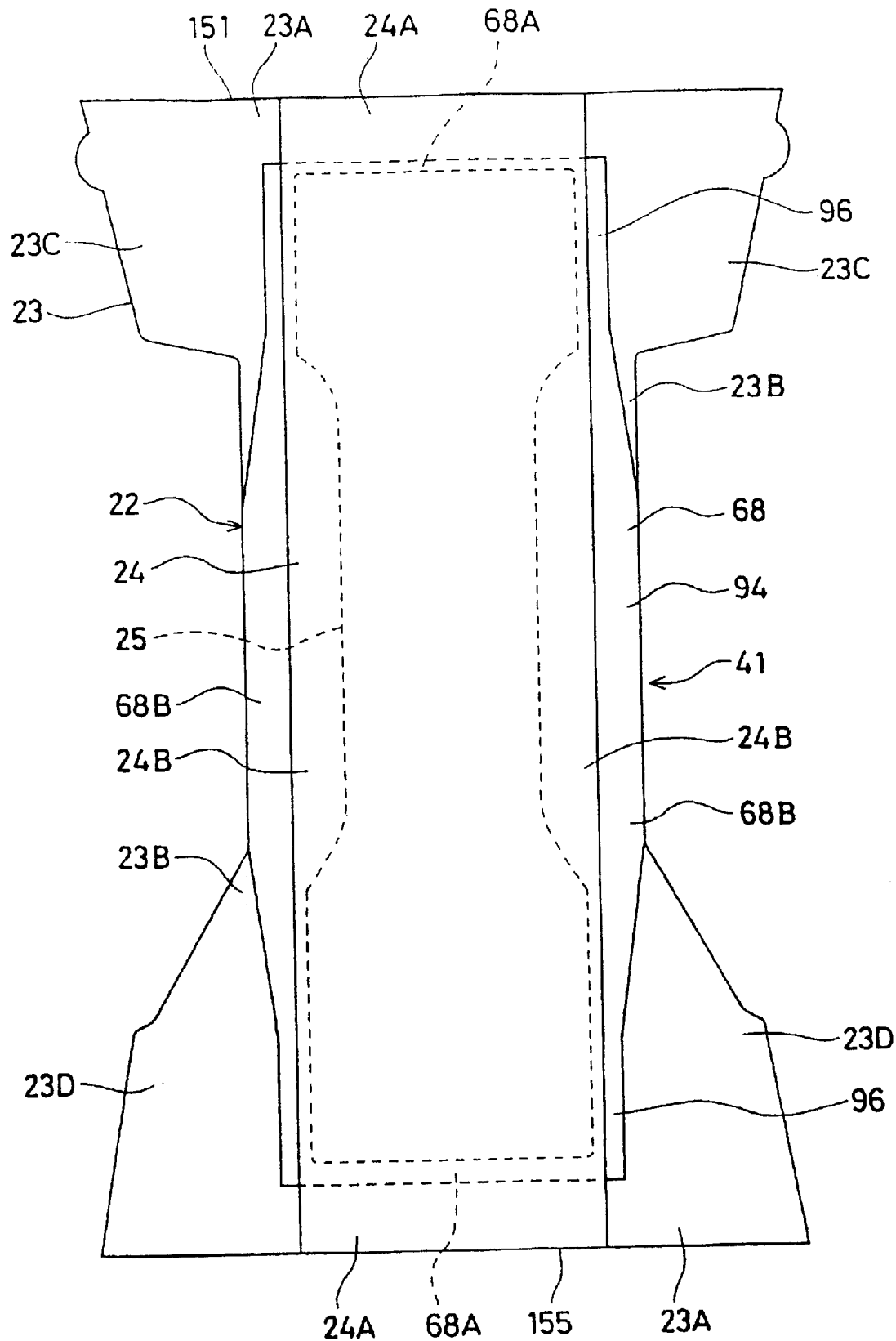
FIG. 4 is a schematically simplified plan view of the embodiment of FIG. 3, showing a chassis comprising a topsheet, a backsheet and an absorbent core therebetween, eliminating the other elements of the pull-on garment.

The chassis 41, referring to FIGS. 3 and 4, the chassis 41 comprises an absorbent core 25 and a plurality of layers disposed in association with the absorbent core 25, such as a topsheet 24 and a backsheet 22 associated with the topsheet 24. The absorbent core 25 is disposed between the topsheet 24 and the backsheet 22. The chassis 41 further may include one or more additional layers disposed associated with the absorbent core 25. The topsheet 24 has the body-facing surface which is positioned adjacent to the wearer's body during use. The backsheet 22 has the outer-facing surface which is positioned away from the wearer's body. Preferably, the backsheet 22 comprises a inner barrier film 68 and a nonwoven outer cover 23. Since the chassis 41 defines the front region 26, the back region 28, and crotch region 30, the chassis 41 also has corresponding regions and panels as previously defined. (For simplicity, these regions and panels are denoted in the drawings by the same reference numerals as the corresponding pull-on diaper regions and panels as shown in FIG. 2.)

The topsheet 24 and the inner barrier film 68 of the backsheet 22 have length and width dimensions generally larger than those of the absorbent core 25. The topsheet 24 and the inner barrier film 68 extend beyond the side edges and end edges of the absorbent core 25 to thereby form the periphery of the chassis 41. The topsheet 24 longitudinally extends between the waist edge 151 and 155 of the pull-on diaper 20. The topsheet 24 has waist end portions 24A and side portions 24B. The waist end portions 24A (i.e., end extended portion 24A) of the topsheet 24 extend into a portion of the waistband panel 6 and 7 of the pull-on diaper 20. The inner barrier film 68 has waist end portions 68A and side portions 68B. The inner barrier film 68 is a little shorter in the longitudinal direction than the topsheet 24 and a little wider in the lateral direction than the topsheet 24. The inner barrier film 68 has a nonuniform lateral width so as to form a first portion 94 in at least a portion of the crotch region 30 and a second portion 96 in at least a portion of the front or back region 26 and 28. The lateral width of the inner barrier film 68 gradually decreases towards the waist end portions 68A such that the second portion 96 has a lateral width dimension less than the lateral width dimension of the first portion 94. The inner barrier film 68 does not preferably extend into the ear panel 10 and 11 so as to increase the effective lateral extended length of the ear panel 10 and 11 and reduce bulkiness of the ear panel 10 and 11. The inner barrier film 68 also does not extend into the waistband panel 6 and 7 so as to reduce bulkiness of the waistband panel 6 and 7. In addition, since the inner barrier film 68 does not extend into both the ear panel 10 and 11 and the waistband panel 6 and 7, the inner barrier film 68 does not inhibit breathability in those areas. While the topsheet 24, the inner barrier film 68, and the absorbent core 25 may be assembled in a variety of well known configurations, exemplary chassis configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

Preferably, the nonwoven outer cover 23 covers almost all of the area of the outermost portion of the pull-on diaper 20. The nonwoven outer cover 23 may have generally the same shape as the pull-on diaper 20. The nonwoven outer cover 23 has waist end portions 23A and side portions 23B. The nonwoven outer cover 23 also has a side extended portion 23C in the front region 26 and a side extended portion 23D in the back region 28. The waist end portion 23A (i.e., end extended portion 23A) of the nonwoven outer cover 23 extends into the waistband panel 6 and 7, and the side extended portion 23C and 23D of the nonwoven outer cover 23 extends into the ear panel 10 and 11. Alternatively, the nonwoven outer cover 23 of the backsheet 22 may have generally same shape as the inner barrier film 68 such that the nonwoven outer cover 23 covers only the area of the inner barrier film 68. Alternatively, the nonwoven outer cover 23 may be eliminated, and the inner barrier film 68 may have generally the same shape as the pull-on diaper 20 and extend into both ear panel 10 and 11 and waistband panel 6 and 7.

The absorbent core 25 may be any absorbent member which is generally compressible, conformable, non-irritating to the wearer's skin, and capable of absorbing and retaining liquids such as urine and other certain body exudates. The absorbent core 25 may be manufactured in a wide variety of sizes and shapes (e.g., rectangular, hourglass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may comprise one or more layers or structures). Further, the size and absorbent capacity of the absorbent core 25 may also be varied to accommodate wearers ranging from infants through adults. However, the total absorbent capacity of the absorbent core 25 should be compatible with the design loading and the intended use of the diaper 20.

The absorbent core 25 in a preferred embodiment has an asymmetric, modified hourglass-shape having ears in the front and back waist regions 26 and 28. Other exemplary absorbent structures for use as the absorbent core 25 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

Figure 5:
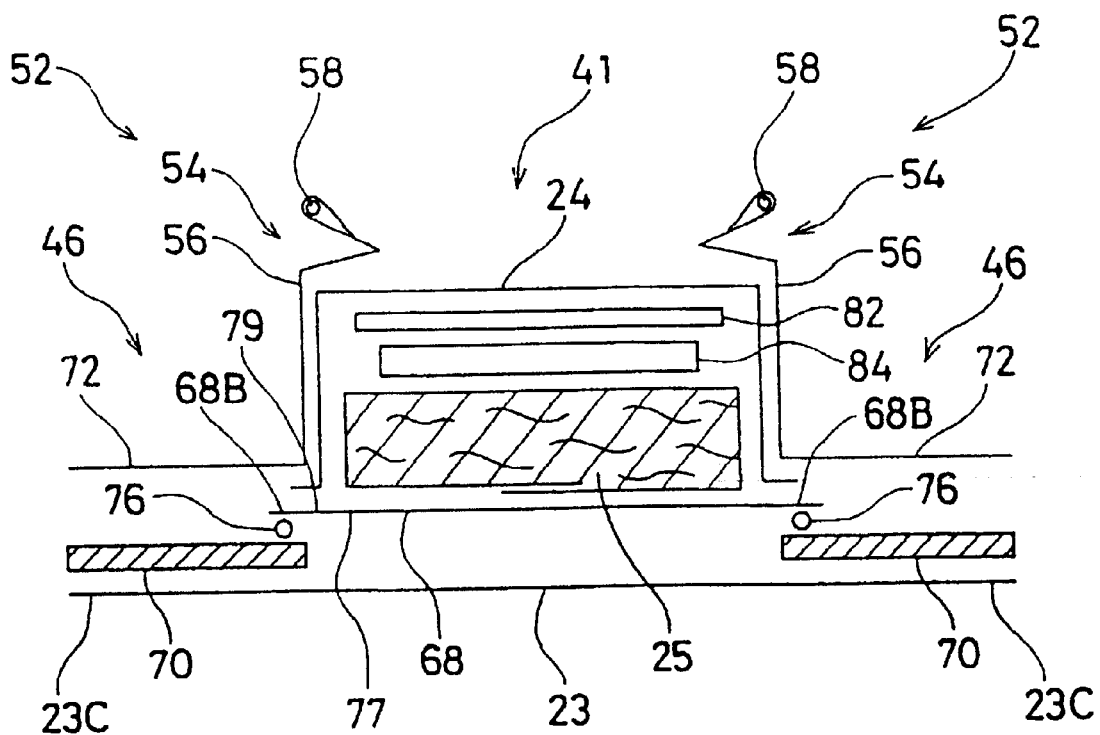
FIG. 5 is a cross-sectional view of a preferred embodiment taken along the section line 4—4 of FIG. 3.

The chassis 41, as shown in FIG. 5, may further include an acquisition/distribution core 84 of chemically stiffened fibers positioned over the absorbent core 25, thereby forming a dual core system. Preferred dual core systems are disclosed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. In a preferred embodiment, the acquisition/distribution core 84 comprise chemically treated stiffened cellulosic fiber material, available from Weyerhaeuser Co. (U.S.A.) under the trade designation of CMC.

More preferably, the chassis 41 may further include an acquisition/distribution layer 82 between the topsheet 24 and the acquisition/distribution core 84 as shown in FIG. 5. The acquisition/distribution layer 82 is provided to help reduce the tendency for surface wetness of the topsheet 24. The acquisition/distribution layer 82 preferably comprises carded, resin bonded hiloft nonwoven materials such as, for example, available as Code No. FT-6860 from Polymer Group, Inc., North America (Landisiville, N.J., U.S.A.), which is made of polyethylene terephthalate fibers of 6 dtex, and has a basis weight of about 43 g/m$^{2.}$ The topsheet 24 is preferably compliant, soft feeling, and non-irritating to the wearer's skin. Further, the topsheet 24 is liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 25 (i.e., to prevent rewet). If the topsheet 24 is made of a hydrophobic material, it is preferable that at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 25. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991. The topsheet 24 may be compatible with ventilation design/process preferably along the waistband panel 6 and 7 and other portions on the pull-on diaper 20.

In preferred embodiments, the topsheet 24 is a nonwoven web that can provide reduced tendency for surface wetness; and consequently facilitate maintaining urine absorbed by the absorbent core 25 away from the user's skin, after wetting. One of the preferred topsheet materials is a thermobonded carded web which is available as Code No. P-8 from Fiberweb North America, Inc. (Simpsonville, S.C., U.S.A.). Another preferred topsheet material is available as Code No. S-2355 from Havix Co., Japan. This material is a bi-layer composite material, and made of two kinds of synthetic surfactant treated bicomponent fibers by using carding and air-through technologies. Yet another preferred topsheet material is a thermobonded carded web which is available as Code No. Profleece Style 040018007 from Amoco Fabrics, Inc. (Gronau, Germany).

Another preferred topsheet 24 comprises an apertured formed film. Apertured formed films are preferred for the topsheet 24 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No 4,324,246 entitled "Disposable Absorbent Article Having A Stain Resistant Topsheet", which issued to Mullane, et al. on Apr. 13, 1982; U.S. Pat. No 4,342,314 entitled "Resilient Plastic Web Exhibiting Fiber-Like Properties", which issued to Radel et al. on Aug. 3, 1982; U.S. Pat. No 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9,1991.

The backsheet 22 preferably comprises a inner barrier film 68 and a nonwoven outer cover 23. The inner barrier film 68 is preferably impervious to liquids (e.g., urine) and is preferably manufactured from a thin plastic film. The inner barrier film 68 has a body-facing surface 79 and an outer-facing surface 77. More preferably the plastic film permits vapors to escape from the diaper 20. In a preferred embodiment, a microporous polyethylene film is used for the inner barrier film 68. A suitable microporous polyethylene film is manufactured by Mitsui Toatsu Chemicals, Inc., Nagoya, Japan and marketed in the trade as Espoir No. The backsheet 22 is preferably compatible with ventilation and side seaming design/process. A disposable tape may be further joined to the outer surface of the backsheet.

A suitable plastic film material for the inner barrier film 68 is a thermoplastic film having a thickness of from about 0.012 mm (0.5 mil) to about 0.051 mm (2.0 mils), preferably comprising polyethylene or polypropylene. Preferably, the plastic film has a basis weight of from about 5 g/m$^2$ to about 35 g/m$^2$. However, it should be noted that other flexible liquid impervious materials may be used. Herein "flexible" refers to materials which are compliant and which will readily conform to the general shape and contours of the wearer's body. The plastic film may have moisture vapor transmission rate of between 3,000 and 4,000 g/m$^2$/24 hr which is measured by a method set forth below.

The nonwoven outer cover 23 is joined with the outer-facing surface of the inner barrier film 68 to form a laminate (i.e., the backsheet 22). The nonwoven outer cover 23 is positioned at the outermost portion of the pull-on diaper 20 and covers at least a portion of the outermost portion of the diaper 20. The nonwoven outer cover 23 may be joined to the inner barrier film 68 by any suitable attachment means known in the art. For example, the nonwoven outer cover 23 may be secured to the inner barrier film 68 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H. B. Fuller Japan Co., Ltd., Osaka, Japan as JM-6064.

In a preferred embodiment, the nonwoven outer cover 23 is a carded nonwoven web, for example, obtainable from Havix Co., LTD., Gifu, Japan as E-2341. The nonwoven outer cover 23 is made of bi-component fibers of a polyethylene (PE) and a polyethylene terephthalate (PET). The ratio of PE/PET is about 40/60. The PE/PET bi-component fiber has the dimension of 2 decitex×51 mm. Another preferred carded nonwoven web is obtainable from Chisso Corp., Osaka, Japan. The nonwoven outer cover 23 is also made of bi-component fibers of a polyethylene (PE) and a polyethylene terephthalate (PET). The ratio of PE/PET is about 30/70.

In another preferred embodiment, the nonwoven web is a spunbonded nonwoven web, for example, obtainable from Mitsui Petrochemical Industries, Ltd., Tokyo, Japan. The nonwoven web is made of bi-component fibers consisting of a polyethylene (PE) sheeth and a polypropylene (PP) core. The ratio of PE/PP is about 80/20. The PE/PP bi-component fiber has the thickness of approximately 2.3 decitex.

The backsheet 22 is preferably positioned adjacent the outer-facing surface of the absorbent core 25 and is preferably joined thereto by any suitable attachment means known in the art. For example, the backsheet 22 may be secured to the absorbent core 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No 3,911,173 issued to Sprague, Jr. on Oct. 7, 1975; U.S. Pat. No 4,785,996 issued to Ziecker, et al. on Nov. 22, 1978; and U.S. Pat. No 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

In an alternative embodiment, the absorbent core 25 is not joined to the backsheet 22, and/or the topsheet 24 in order to provide greater extensibility in the front region 26 and the back region 28.

The elasticized leg cuffs 52 provides improved containment of liquids and other body exudates. The elasticized leg cuffs 52 may comprise several different embodiments for reducing the leakage of body exudates in the leg regions. (The leg cuff can be and is sometimes also referred to as leg bands, side flaps, barrier cuffs, or elastic cuffs.) U.S. Pat. No 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No 4,695,278 entitled "Absorbent Article Having Dual Cuffs" issued to Lawson on Sep. 22, 1987; and U.S. Pat. No 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No 4,704,115 entitled "Disposable Waist Containment Garment" issued to Buell on Nov. 3, 1987, discloses a disposable diaper or incontinence garment having side-edge-leakage-guard gutters configured to contain free liquids within the garment.

While each elasticized leg cuff 52 may be configured so as to be similar to any of the leg bands, side flaps, barrier cuffs, or elastic cuffs described above, it is preferred that each elasticized leg cuff 52 comprises inner barrier cuffs 54 each comprising a barrier flap 56 and a spacing means 58 (as shown in FIG. 5) as described in the above-referenced U.S. Pat. No 4,909,803. The inner barrier cuffs 54 may have an insert element which is highly impermeable, but preferably breathable. In a preferred embodiment, the elasticized leg cuff 52 additionally comprises an elastic gasketing cuff 62 with one or more elastic strands 64, positioned outboard of the barrier cuff 54 such as described in the above-referred U.S. Pat. Nos. 4,695,278 and 4,795,454. The elastic strands 64 are generally disposed in the leg flap panel 4 and joined to thereto by any means such as hot melt glue under a prestrained condition. The elastic strands 64 may be prestrained, before being joined, up to between 30% and 200%, preferably between 50% and 150%. A preferred elastic strands 64 is manufactured by Fulflex International Company under the designation 9312.

The pull-on diaper 20 has the front extensible ear 46 and the back extensible ear 48. Referring to FIG. 5, the extensible ear 46 and 48 preferably comprises a side elastic member 70 having a side elastomeric material 124 (shown in FIG. 8), the side extended portion 23C of the nonwoven outer cover 23, and an extended portion 72 of the inner barrier cuff 54 (although FIG. 5 depicts only the structures in the front region 26, preferably the structures in the back region 28 are the same or similar to those in the front region 26). Preferably at least one of the front and back extensible ears 46 and 48 is elastically extensible in at least the lateral direction. More preferably, both the front and the back extensible ears 46 and 48 are elastically extensible in at least the lateral direction. In an alternative embodiment, the front and back extensible ear 46 and 48 is elastically extensible both in the lateral and longitudinal directions. Herein "extensible" refers to materials that are capable of extending in at least one direction to a certain degree without undue rupture. Herein "elasticity" and "elastically extensible" refer to extensible materials that have the ability to return to approximately their original dimensions after the force that extended the material is removed. Herein any material or element described as "extensible" may also be elastically extensible unless otherwise provided. The extensible ear 46 and/or 48 provides a more comfortable and contouring fit by initially conformably fitting the diaper to the wearer and sustaining this fit throughout the time of wear well past when the diaper has been loaded with exudates since the extensible ear 46 and/or 48 allows the sides of the diaper to expand and contract.

The extensible ear 46 and 48 preferably has breathability. The moisture vapor transmission rate of the ear panel in conjunction with the overall vapor transmission rate of the rest of the pull-on diaper is important in reducing the incidence of heat rash and other skin problems associated with high heat humidity conditions. In order to reduce humidity and heat humidity within the pull-on diaper, the extensible ear 46 and 48 preferably has a weighed average mass vapor transmission rate of at least about 2,000 g/m²/24 hr, more preferably at least 4,000 g/m²/24 hr. Preferably, the entire pull-on diaper has a weighed average mass vapor transmission rate of from at least 2,000 g/m²/24 hr to about 8,000 g/m²/24 hr.

The moisture vapor transmission rate is measured by the method set forth below. A known amount of $CaCl_2$ is put into a flanged cup. A sample is placed on the top of the cup and held securely by a retaining ring and gasket. The assembly is then weighed and recorded as the initial weight. The assembly is placed in a constant temperature (40° C.) and humidity (75% RH) chamber for 5 hours. The assembly is then removed from the chamber and allowed to equilibrate for at least 30 minutes at the temperature of the room where the balance is located. The assembly is then weighed and recorded as the final weight. The mass vapor transmission rate (MVTR) is calculated and expressed in g/m²/24 hr using the following formula.

$$MVTR = \frac{(Final\ weight - Initial\ weight) \times 24.0}{Area\ of\ sample\ in\ meters \times 5.0\ (time\ in\ chamber)}$$

Figure 6:
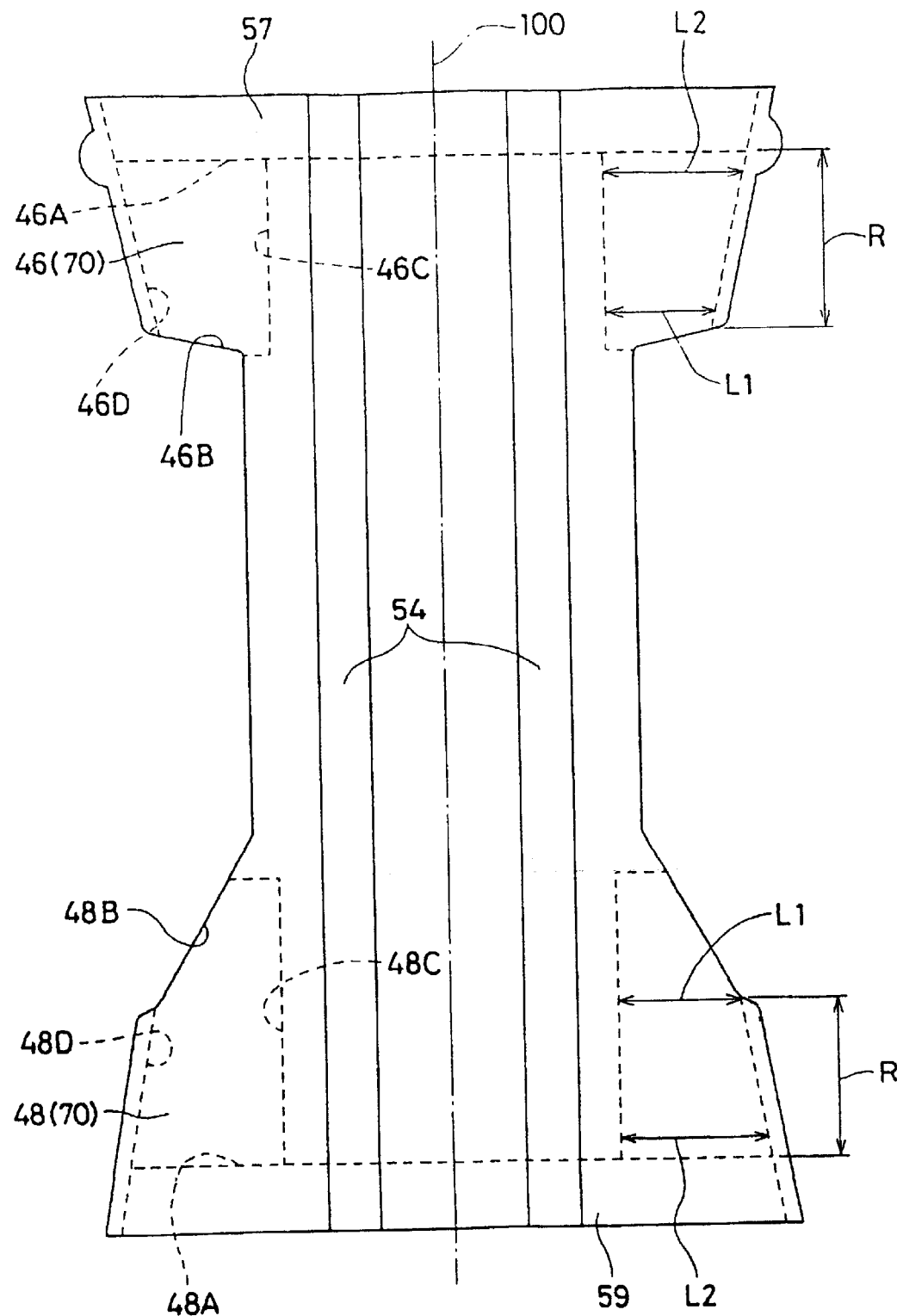
FIG. 6 is a schematically simplified plan view of the embodiment of FIG. 3, showing the disposable pull-on garment having an extensible ear and an extensible waistband.

Referring to FIG. 6 as well as FIG. 3, the extensible ear 46 comprising the side elastic member 70 has a higher end edge 46A, a lower end edge 46B, an inner side edge 46C, and an outer side edge 46D. The back extensible ear 48 comprising the side elastic material 70 has a higher end edge 48A, a lower end edge 48B, an inner side edge 48C, and an outer side edge 48D. Although a configuration of each element, portion, part, etc. in the front region 26 may be different from that in the back region 28 (such as configuration of the front extensible ear 46 and configuration of the back extensible ear 48, or configuration of the lower end edge 46B and configuration of the lower end edge 48B), those elements, portions, parts, etc. which correspond to each other in the front region 26 and in the back region 28 may be described concurrently for ease of description. In a preferred embodiment, the ear panel 10 and 11 is rendered extensible in the entire area of the ear panel 10 and 11 to form the extensible ear 46 and 48 by the side elastic material 70. In the embodiment shown in FIG. 3, the side elastic material 70 extends into a part of the seam panel 12 and 13 so that the front extensible ear 46 and the back extensible ear 48 are anchored each other at the seam 32, and the side elastic material 70 in the front region 26 and the side elastic material 70 in the back region 28 are anchored at the seam 32 (FIG. 5 also shows the side elastic member 70 which extends into the seam panel 12 and 13, though the seam panel 12 and 13 is not shown in FIG. 5). Alternatively, the ear panel 10 and 11 may be rendered extensible only in a portion of the area in the ear panel 10 and 11. The extensible ear 46 and 48 is the part of the ear panel 10 and 11 rendered extensible by joining the side elastic member 70 and being subjected to mechanical stretching. In a preferred embodiment, the inner side edge 46C and 48C extends generally along the longitudinal center line 100 of the pull-on diaper 20. The outer side edge 46D and 48D is non-parallel to the inner side edge 46C and 48C and is non-parallel to the longitudinal center line 100. The outer side edge 46D and 48D projects laterally outwardly proximate the higher end edge 46A and 48A. Therefore, the outer side edge 46D and 48D remotes from the inner side edge 46C and 48C proximate the higher end edge 46A and 48A. The extensible ear 46 and 48 has a lateral width L1 between the inner side edge 46C and 48C and the outer side edge 46D and 48D proximate the lower end edge 46B and 48B, and a lateral width L2 between the inner side edge 46C and 48C and the outer side edge 46D and 48D proximate the higher end edge 46A and 48A. The lateral width between the inner side edge and the outer side edge is the width between the inner side edge 46C and 48C and the outer side edge 46D and 48D in the lateral direction perpendicular to the longitudinal center line 100. Therefore, the lateral width between the inner side edge and the outer side is available in the range R where the inner side edge 46C and 48C and the outer side edge 46D and 48D co-extend in the longitudinal direction. The lateral width L2 is greater than the lateral width L1, therefore, the available elastomeric material quantity in the lateral direction of the extensible ear 46 and 48 is greater proximate the higher end edge 46A and 48A than proximate the lower end edge 46B and 48B. Because the outer side edge 46D and 48D projects laterally outwardly proximate the higher end edge 46A and 48A, available elastomeric material quantity proximate the higher end edge 46A and 48A is enhanced. Further, the available elastomeric material quantity changes in the direction from the higher end edge 46A and 48A toward the lower end edge 46B and 48B because the lateral width of the extensible ear 46 and 48 gradually changes in that direction. This results in change of forces or force gradient over the extensible ear allowing for custom fit. The inner side edge 46C and 48C also may be non-parallel to the longitudinal center line 100 and project laterally inwardly proximate the higher end edge 46A and 48A such that the lateral width L2 becomes further greater than the lateral width L1. Alternatively, the inner side edge 46C and 48C may project a little laterally outwardly proximate the higher end edge 46A and 48A such that the lateral width L2 is still greater than the lateral width L1.

The extensible ear 46 and 48 may be formed by unitary elements of the pull-on diaper 20 (i.e., they are not separately manipulative elements secured to the pull-on diaper 20, but rather are formed from and are extended portions of one or more of the various layers of the pull-on diaper). In a preferred embodiment, the extensible ear 46 and 48 is a projected member of the chassis 41. Preferably, the extensible ear 46 and 48 comprises at least one unitary element or a continuous sheet material that forms a part of the chassis 41 and continuously extends to the extensible ear 46 and 48. Alternatively, the extensible ear 46 and 48 may be discrete members which do not have any unitary element that forms a part of the chassis 41. The extensible ear 46 and 48 may be formed by joining the discrete members to the side portions of the chassis 41.

The side elastic member 70 is interposed between the extended portion 72 of the inner barrier cuff 54 and the side extended portion 23C and 23D of the nonwoven outer cover 23 in the region of the extensible ear 46 and 48. The side elastic member 70 is operatively joined to at least one of the extended portion 72 of the inner barrier cuff 54 and the side extended portion 23C and 23D of the nonwoven outer cover 23. Preferably, the side elastic member 70 is operatively joined to both the extended portion 72 of the inner barrier cuff 54 and the side extended portion 23C and 23D of the nonwoven outer cover 23 while in a substantially untensioned (zero strain) condition.

The side elastic member 70 can be operatively joined to the inner barrier cuff 54 and the nonwoven outer cover 23, by using either an intermittent bonding configuration or a substantially continuous bonding configuration. Herein an "intermittently" bonded laminate web means a laminate web wherein the plies are initially bonded to one another at discrete spaced apart points or a laminate web wherein the plies are substantially unbonded to one another at discrete spaced apart areas. Conversely, a "substantially continuously" bonded laminate web means a laminate web wherein the plies are initially bonded substantially continuously to one another throughout the areas of interface. Because it is preferred that the stretch laminate be bonded over all or a significant portion of the stretch laminate so that the inelastic webs (i.e., nonwoven webs of the inner barrier cuff 54 and the nonwoven outer cover 23) elongate or draw without causing rupture, and the layers of the stretch laminates are preferably bonded in a configuration that maintains all of the layers of the stretch laminate in relatively close adherence to one another after the incremental mechanical stretching operation, the side elastic member and the other plies of the stretch laminate are substantially continuously bonded together using an adhesive. In a particularly preferred embodiment, the adhesive selected is applied in a spiral pattern (such as is shown in U.S. Pat. No. 3,911,173 (Sprague, Jr.) and U.S. Pat. No. 4,842,666 (Werenicz)) at a basis weight of about 0.116 g/m². The spirals have a width of about 1.9 cm (0.75 in) and either are positioned just next to each other or overlap slightly (less than 2 mm). The adhesive is preferably an adhesive such as is available from Findley Adhesives under the designation H2120. Alternatively, the side elastic member and any other components of the stretch laminates may be intermittently or continuously bonded to one another using heat bonding, pressure bonding, ultrasonic bonding, dynamic mechanical bonding, or any other method as is known in the art.

After the side elastic member 70 is operatively joined to the extended portion 72 of the inner barrier cuff 54 and the side extended portion 23C and 23D of the nonwoven outer cover 23, at least a portion of the resultant composite stretch laminate is then subjected to mechanical stretching sufficient to permanently elongate the non-elastic components which are, for example, the extended portion 72 of the inner barrier cuff 54 and the side extended portion 23C and 23D of the nonwoven outer cover 23. The composite stretch laminate is then allowed to return to its substantially untensioned condition. The extensible ear 46 and 48 is thus formed into "zero strain" stretch laminates. (Alternatively, the side elastic member 70 could be operatively joined in a tensioned condition and then subjected to mechanical stretching.) Herein "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial mechanical stretching. Particularly preferred methods and apparatus used for making stretch laminates utilize meshing corrugated rolls or plates to mechanically stretch the components. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1990; U.S. Pat. No 5,143,679 issued to Weber et al. on Sep. 1, 1992 and European Pat. Application No. 98108290.2 titled "METHOD AND APPARATUS FOR ACTIVATING A MOVING WEB" filed on May 7, 1998 (Christoph J. Schmitz et al.).

The side elastic member 70 is preferably joined to, more preferably directly secured to the side portions 68B of the inner barrier film 68 through an adhesive 76 as shown in FIG. 5. In a preferred embodiment, the side elastic member 70 is joined to the side portions 68B of the inner barrier film 68 at the outer-facing surface 77. In an alternative embodiment, the side elastic member 70 may be joined to the side portions 68B of the inner barrier film 68 at the body-facing surface 79. Preferably, the adhesive 76 is applied as an bead. The adhesive 76 may be applied as a spiral. In a preferred embodiment, the adhesive 76 is a flexible adhesive with an amorphous and crystallizing component. Such a preferred adhesive is supplied by the Findley Adhesive Company under the designation #H9224. Alternatively, the side elastic member 70 may be joined to the side portions 68B of the inner barrier film 68 by any other bonding means known in the art which comprise heat bonds, pressure bonds, ultrasonic bonds, dynamic mechanical bonds, or combinations of these attachment means.

Figure 8:
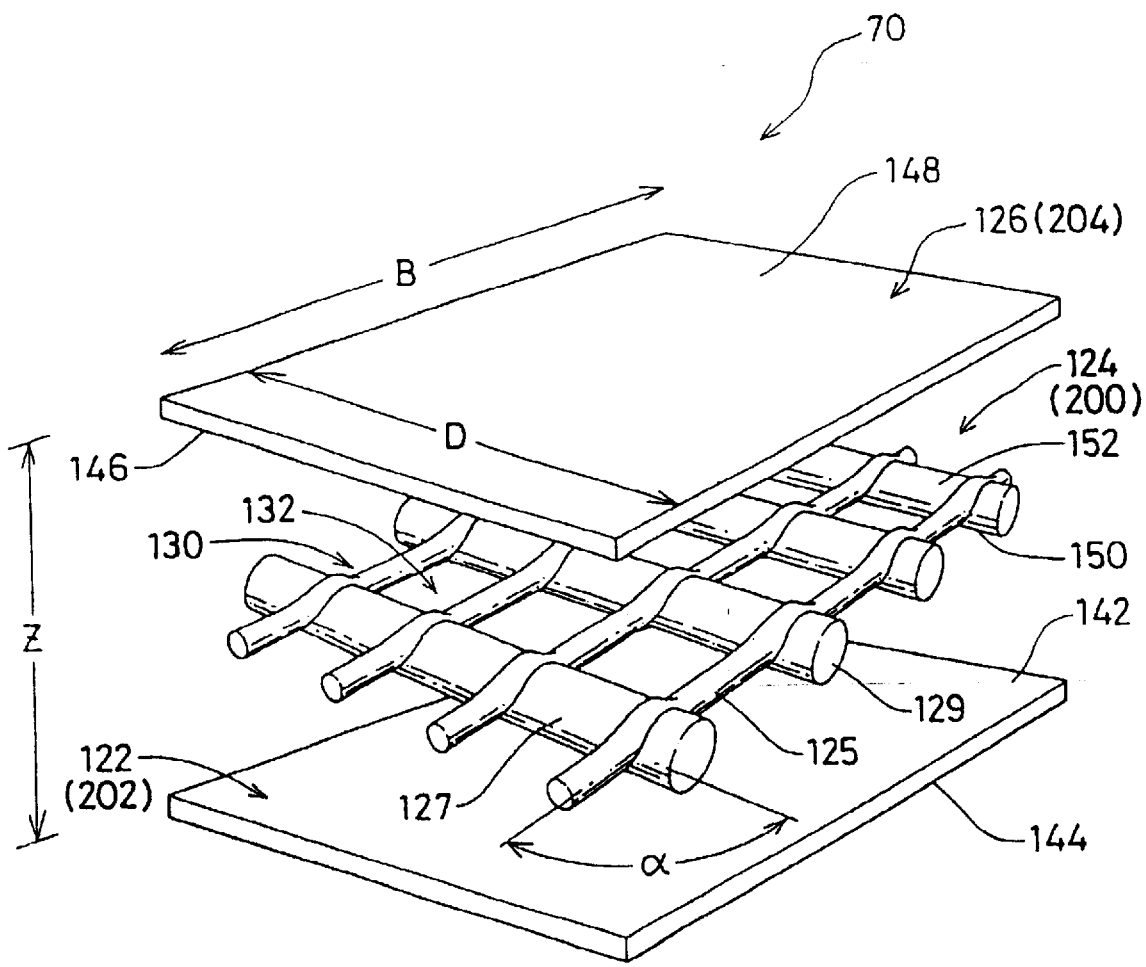
FIG. 8 is a cross-sectional perspective view of an elastic member of a preferred embodiment.

The side elastic member 70 used for extensible ear 46 and 48, referring to FIG. 8, comprises the side elastomeric materiar 124. The side elastic material 70 may further include one of, preferably both of a first coverstock layer 122 and a second coverstock layer 126. Alternatively, the side elastic material 70 may not include any additional layer.

The side elastomeric material 124 has a first surface 150 and a second surface 152 opposing the first surface 150, and a first coverstock layer 122 which is joined to the first surface 150 of the side elastomeric material 124. In a preferred embodiment, the first coverstock layer 122 is joined to the first surface 150 of the side elastomeric material 124 by an adhesive 160 as shown, for example, in FIG. 9. More preferably, the side elastic member 70 further comprises a second coverstock layer 126 which is joined to the second surface 152 of the side elastomeric material 124 by an adhesive 164. The side elastomeric material 124 provides a good fitness by generating the optimal retention (or sustained) force at the side area of the wearer. Preferably, the side elastomeric material 124 is extensible in at least one direction, preferably in a direction having a vector component in the lateral direction to generate a retention (or sustained) force that is optimal to prevent the pull-on diaper 20 from drooping, sagging, or sliding down from its position on the torso without causing the red marking on the skin of the wearer.

The side elastomeric material 124 may, be formed in a wide variety of sizes, forms and shapes. In a preferred embodiment, the side elastomeric material 124 is in the form of a continuous plane layer. Preferred forms of continuous plane layer include a scrim, a perforated (or apertures formed) film, an elastomeric woven or nonwoven, and the like. In an alternative embodiment, the side elastomeric material 124 is in the form of strands (or strings) which are not connected each other to form a continuous plane layer. The continuous plane layer may take any shape which can be suitably provided in the ear panels. Preferred shapes of continuous plane layer include a quadrilateral including a rectangle and a square, a trapezoid, and the other polygons.

Elastomeric materials which have been found to be especially suitable for the side elastomeric material 124 are styrenic block copolymer based scrim materials, perforated (or apertured) elastic films, strands, preferably with a thickness of from about 0.05 mm to about 1.0 mm (0.002 inch–0.039 inch). Other suitable elastomeric materials for the side elastomeric material 124 include "live" synthetic or natural rubber, other synthetic or natural rubber foams, elastomeric films (including heat shrinkable elastomeric films), elastomeric woven or nonwoven webs, elastomeric composites, or the like.

The extensibility properties of the side elastomeric material 124 such as the First Cycle Extension Force at 100% Extension (FCEF100%), the First Cycle Extension Force at 200% Extension (FCEF200%), the Second Cycle Recovery Force at 50% Extension (SCRF50%) and sustained load at 50% after 10–12 hours are important considerations in the performance of disposable garments. The side elastomeric material 124 preferably has extensibility properties within the defined ranges herein. The FCEF100% and the FCEF200% are measures of the overall perceived "stretchiness" during application/removal of disposable garments. These two properties also effect the ability of the applicator to achieve a suitable degree of application stretch. A side elastomeric material 124 with a relatively high FCEF100% and FCEF200% can cause difficulty in applying the disposable garment onto the wearer. On the other hand, a side elastomeric material 124 with a relatively low FCEF100% and FCEF200% may not achieve a suitable level of body fiting/conformity. The SCRF50% also closely relates to the body fitting/conformity of disposable garments for the wearer. A side elastomeric material 124 with a relatively high SCRF50% tends to cause red marking on the skin of the wearer and may be uncomfortable for the wearer during usage. A side elastomeric material 124 with a relatively low SCRF50% may not provide enough elastic force to keep the diaper in place on the wearer or may not provide good body fit. The sustained load at 50% evaluates the force decay over time. This should be limited or substantial sagging will result.

The values of FCEF100%, FCEF200% and SCRF50% can be measured by using a tensile tester. The tensile tester comprises an upper jaw and a lower jaw which is located below the upper jaw. The upper jaw is movable and is connected to an extension force measuring means. The lower jaw is fixed on a desk (or floor). A test specimen (i.e., the elastomeric material to be measured) which has about 2.54 cm (1.0 inch) in width and about 12.75 cm (5 inches) in length is prepared and clamped between the upper jaw and the lower jaw so that the effective specimen length (L) (i.e., gauge length) is about 2.54 cm (1.0 inch). The extension force is applied to the test specimen through the upper jaw. When no extension force is applied to the test specimen, the test specimen is in its untensioned length. A tensile tester suitable for use herein is available from Instron Corporation (100 Royall Street, Canton, Mass. 02021, U.S.A.) as Code No. Instron 5564.

Figure 10:
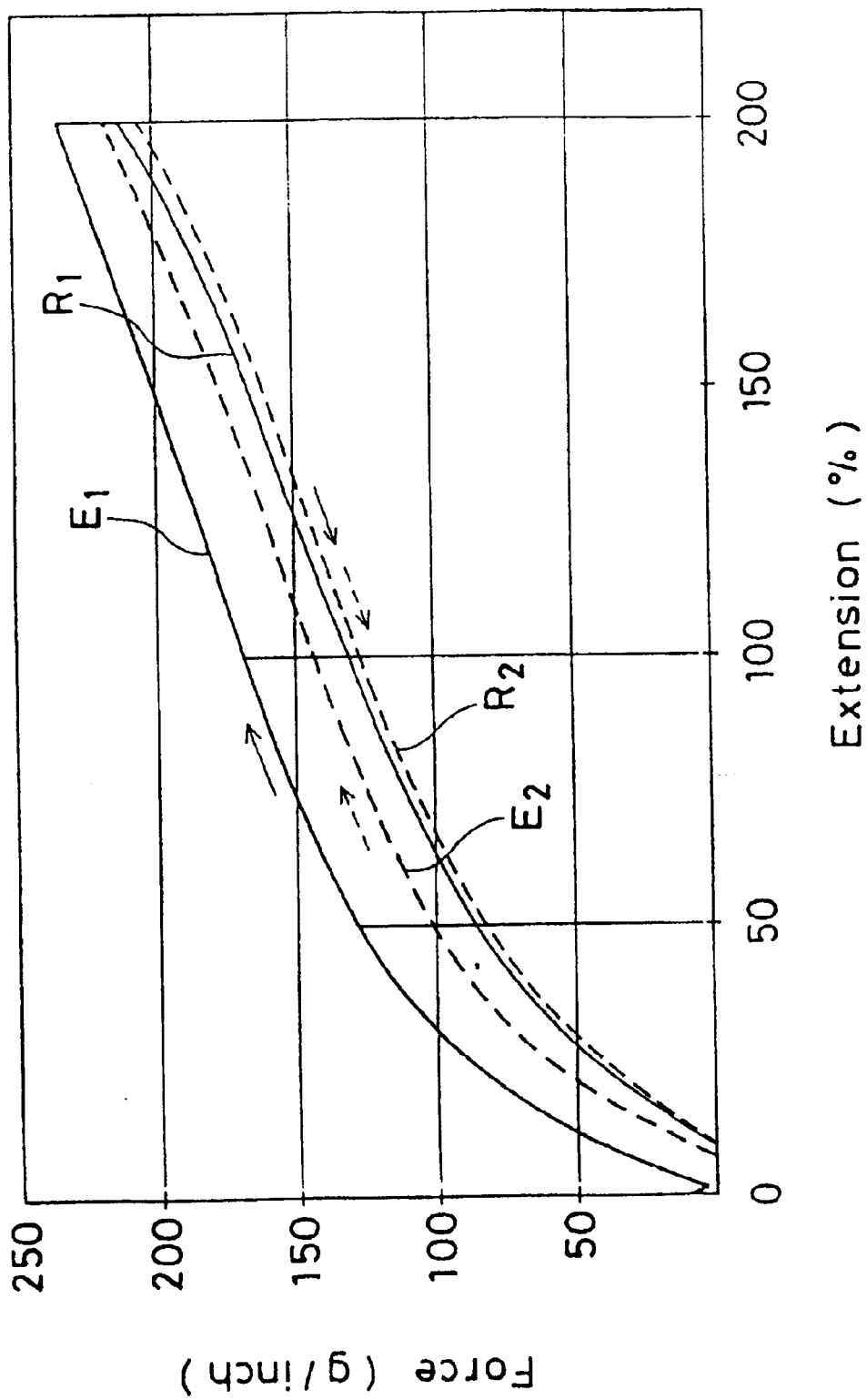
FIG. 10 is a graph showing the two successive cycles of hysteresis curves of an elastomeric material, in a preferred embodiment.

FIG. 10 shows one preferred example of the extension and recovery force curves for the two cycle hysteresis of the side elastomeric material 124. The curve E1 shows the extension force in the first cycle, while the curve R1 shows the recovery force in the first cycle. The curve E2 (shown in dashed lines) shows the extension force in the second cycle, while the curve R2 shows the recovery force in the second cycle. The extension and recovery properties are measured as follows.

In the first cycle, the test specimen is subjected to an initial extension force at a crosshead rate of 25.4 cm/min (10 in/min) at about 23° C. and held for 30 seconds at 200% extension. The test specimen is then allowed to relax at the same rate to the untensioned state. The test specimen is allowed to remain unconstrained for one minute before being subjected to a second extension force (for the second cycle) at the same rate and conditions.

In preferred embodiments, the FCEF100% of the side elastomeric material 124 is at least about 100 grams/inch. More preferably, the FCEF100% is between about 120 to about 220 grams/inch, most preferably between about 150 grams/inch and 190 grams/inch. The FCEF200% is preferably between about 160 grams/inch and about 450 grams/inch, more preferably between about 180 grams/inch and about 300 grams/inch, and yet more preferably between about 200 grams/inch and about 240 grams/inch. The SCRF50% of the side elastomeric material 124 is preferably between about 40 grams/inch and about 130 grams/inch, more preferably between about 65 grams/inch and about 105 grams/inch, and yet more preferably between about 75 grams/inch and about 95 grams/inch. The sustained load at 50% is preferably between about 40 grams/inch and about 130 grams/inch, more preferably between about 65 grams/inch and about 105 grams/inch, and yet more preferably between about 75 grams/inch and about 95 grams/inch.

In the preferred embodiment shown in FIG. 8, the elastomeric scrim 124 has a plurality of first strands 125 and a plurality of second strands 127. The plurality of first strands 125 intersect the plurality of second strands 127 at nodes 130 at a predetermined angle α, forming a net-like open structure having a plurality of apertures 132. Each aperture 132 is defined by at least two adjacent first strands and at least two adjacent second strands, so that the apertures 132 are substantially rectangular in shape. Other configurations of the apertures 132, such as parallelograms, squares, or circular arc segments, can also be provided. Preferably, the first and second strands 125 and 127 are substantially straight and substantially parallel to one another. Preferably, the first strands 125 intersect the second strands 127 at nodes 130 such that the angle α is about 90 degrees. The first and second strands 125 and 127 are preferably joined or bonded at nodes 130. A preferred elastomeric scrim 124 is manufactured by the Conwed Plastics Company under the designation XO2514. This material has about 12 elastic strands per inch in the structural direction B (i.e., the first strands 125) and about 7 elastic strands per inch in the structural direction D (i.e., the second strands 127).

Figure 11:
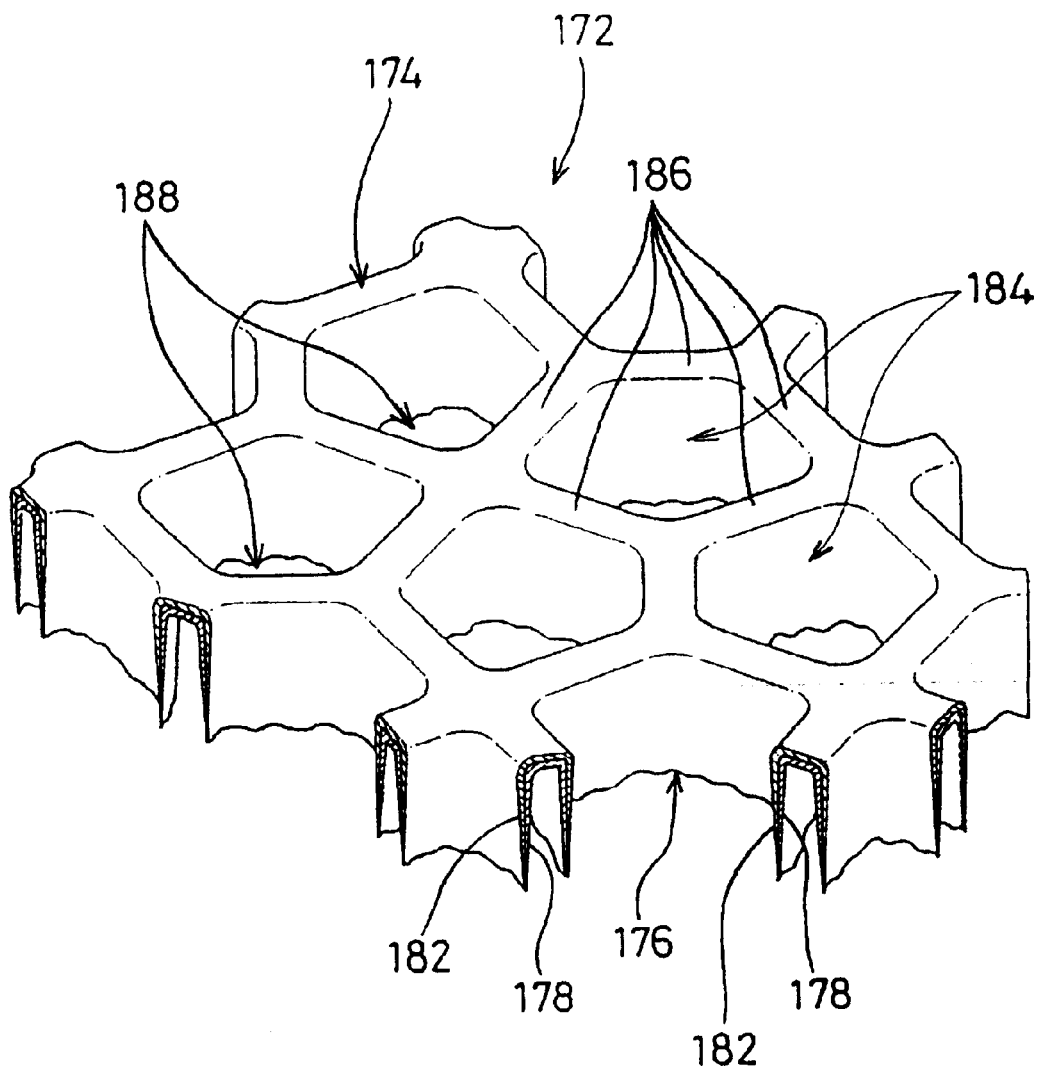
FIG. 11 is an enlarged, partially segmented, perspective view of an alternative embodiment of the elastomeric material.

In another preferred embodiment shown in FIG. 11, the elastomeric material 124 may comprise a porous, macroscopically-expanded, three-dimensional elastomeric web 172. The web 172 has a continuous first surface 174 and a discontinuous second surface 176 remote from first surface 174. The elastomeric web 172 preferably comprises a formed film having at least two polymeric layers, with at least one of the layers being an elastomer layer 178 and at least one of the other layers being a substantially less elastomeric skin layer 182. The elastomeric web exhibits a multiplicity of primary apertures 184 in the first surface 174 of the web 172, the primary apertures 184 being defined in the plane of the first surface 174 by a continuous network of interconnecting members 186. Each interconnecting member 186 exhibits an upwardly concave-shaped cross-section along its length. The interconnecting members 186 terminate substantially concurrently with one another to form a secondary aperture 188 in the plane of the second surface of the web. The detail of such a structure and the method to manufacture is disclosed in U.S. patent application Ser. No. 08/816,106, filed Mar. 14, 1997. A preferred porous elastomeric material 124 is manufactured by the Tredegar Film Products under the designation X-25007. The primary apertures 184 may have any shape. Preferably, the primary aperture 184 has a shape having a major axis and a minor axis perpendicular to said major axis, such as oval shape, and the major axis is oriented generally orthogonal to applied strain-induced stresses.

In the embodiment shown in FIG. 8, the side elastic member 70 comprises first and second coverstock layers 122 and 126, and side elastomeric material 124 disposed in the first and second coverstock layers 122 and 126. The first coverstock layer 122 has an inner surface 142 and an outer surface 144. The inner surface 142 of the first coverstock layer 122 is the surface that is positioned facing the side elastomeric material 124. The second coverstock layer 126 also has an inner surface 146 and an outer surface 148. The inner surface 146 of the second coverstock layer 126 is the surface that is positioned facing the side elastomeric material 124. The side elastomeric material 124 also has two planar surfaces, first surface 150 and second surface 152, each of which is substantially parallel with the planes of the first and second coverstock layers 122 and 126. The first surface 150 is that planar surface of the side elastomeric material 124 that is most closely adjacent with the inner surface 142 of first coverstock layer 122. The second surface 152 is that planar surface of side elastomeric material 124 that is most closely adjacent to the inner surface 146 of the second coverstock layer 126.

Since the side elastic member 70 will be subjected to mechanical stretching before and during use, the first and second coverstock layers 122 and 126 preferably has a relatively high elongation at breaking, and are more preferably stretchable or elongatable, yet more preferably drawable (but not necessarily elastomeric), without undue and preferably without any, tearing or ripping. Further, the first and second coverstock layers 122 and 126 are preferably compliant, soft feeling, and non-irritating to the wearer's skin and give the article the feel and comfort of a cloth garment. Suitable materials for the first and second coverstock layers 122 and 126 can be manufactured from a wide range of materials such as plastic films, apertured plastic films, woven or nonwoven webs of natural fibers (e.g., wood or cotton fibers), synthetic fibers (e.g., polyolefins, polyamides, polyester, polyethylene, or polypropylene fibers), or a combination of natural and/or synthetic fibers, or coated woven or nonwoven webs.

Preferably, each of the first and second coverstock layers 122 and 126 is an identical nonwoven material. An exemplary preferred nonwoven material is manufactured by the FiberWeb Company under the designation DAPP-S tex having a basis weight in the rage of 18–35 g/m². The nonwoven may be consolidated or not consolidated. Preferably, the nonwoven is consolidated for the use of a coverstock layers for an elastomeric scrim. This material has a basis weight in the range of 18–35 g/m² before consolidation and a basis weight in the range of about 40–70 g/m² after consolidation. As used herein, "basis weight" is the weight of one square meter of planar web material. Alternatively, highly strainable nonwoven materials may be used. Alternatively, the first and second coverstock layers 122 and 126 need not be of identical materials, as long as the desired performance requirements, such as elastic performance, softness, flexibility, breathability and durability, are met. As used herein, "consolidated nonwoven material" refers to a nonwoven material that has been gathered or necked under mechanical tension in the structural direction D so that the material can elongate in the structural direction D under low force.

Figure 9:
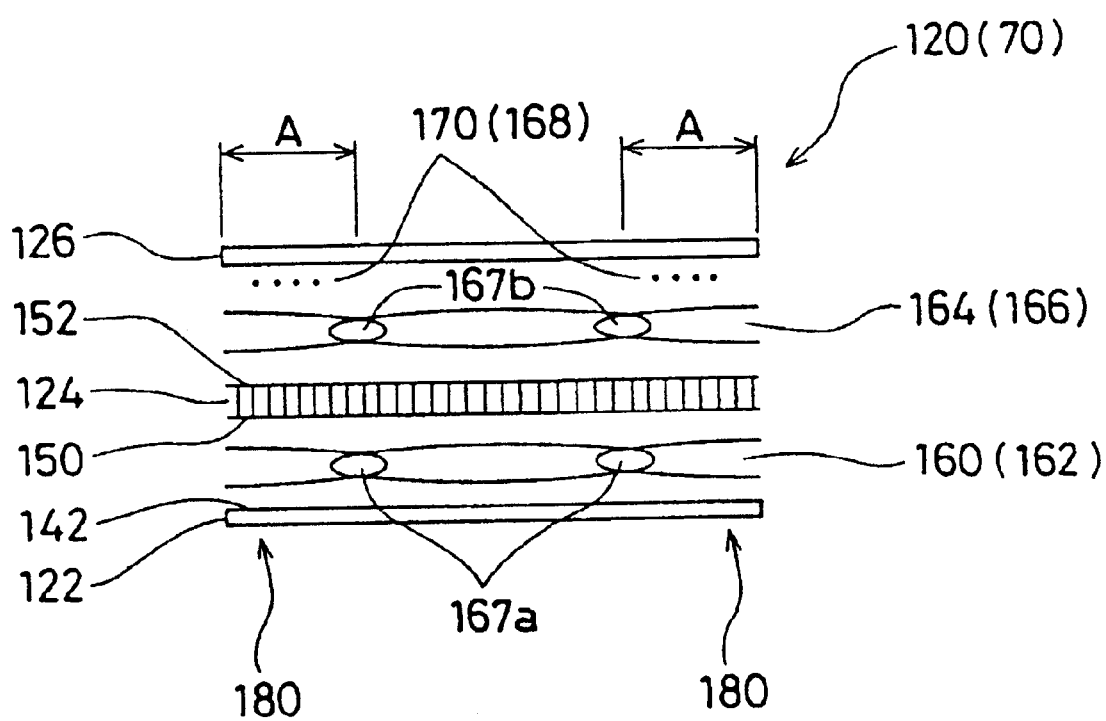
FIG. 9 is a fragmentary enlarged side view of the elastic member shown in FIG. 5.

FIG. 9 shows a fragmentary enlarged side view looking into the structural direction B of the laminate 120 (i.e., the side elastic member 70). It has been found that when the laminate 120 is bonded or otherwise anchored such that side anchor zones A are created, such a laminate 120 is both highly elastic and substantially free from delamination and creep, while providing very good performance characteristics in all performance categories with no trade-offs between any performance characteristics required. The side anchoring is preferably performed by side gluing with adhesive beads to anchor the side elastomeric material 124 between the coverstock layers 122 and 126 as a part of the lamination process. Alternatively, side anchoring may be performed by sewing, heat sealing, ultrasound bonding, needle punching, alternative gluing processes, or by any other means known to those skilled in the art. Another alternative is to side anchor the layers of the laminate structure after the lamination of the elastomeric and coverstock components has been performed.

Preferably, the laminate 120 may particularly provide very good soft feel for the wearer and for the consumer. This is important because consumers value softness. In conventional laminates, the attempts to eliminate creep have frequently required an unacceptable decrease in softness, often accompanied by an unacceptable decrease in the ability to activate. This is because such previous attempts (which have fallen short of eliminating creep) have focused on the application of additional melt blown adhesive, often in an overall coating pattern, in the attempt to strengthen the bonds. This has generally resulted in an undesirable overall stiffening of the laminate. However, the laminates of the preferred embodiments provide elimination of creep without the loss of consumer-desired soft feel and without compromise of activation ability.

Referring to FIG. 9, a first adhesive 170 is applied to the inner surface 146 of the second coverstock layer 126 in positions that correspond to each of the outer portions 180 of the laminate structure 120. The first adhesive 170 may alternatively or additionally be applied to the inner surface 142 of the first coverstock layer 122. For ease of illustration, the description and Figs. refer to application to the second coverstock layer 126 only.

This pattern creates side anchor zones A, which substantially eliminate the delamination and creep associated with previously known laminates and which allows the laminate 120 to experience higher strains without creeping or delaminating. It has also been found that confining the first adhesive 170 to the edge areas 180 of the laminate structure 120 avoids impeding the extensibility of the laminate 120 and also avoids tears in the coverstock layers 122 and 126. Preferably, the first adhesive 170 is applied as a plurality of beads 168, as shown in FIG. 9. Preferably, the first adhesive 170 is a flexible adhesive with an amorphous and crystallizing component. Such a preferred adhesive is made by the Findley Adhesive Company under the designation H9224.

More preferably, the laminate 120 includes a second adhesive 164. The second adhesive 164 is preferably applied to the second surface 152 of the side elastomeric material 124, but could alternatively be applied to the first surface 150 of the elastomeric material 124. The second adhesive 164 is preferably applied in a spiral spray pattern 166, thereby forming bond points 167b that are more discrete than would be formed by a linear spray application. Without being bound by theory, it is believed that most of the second adhesive 164 so sprayed aligns in the structural direction D. Thus, it has been found that spiral spraying results in very good activation properties. As used herein, "activation" refers to the ability to stretch.

It has been found that spraying the layer of second adhesive 164 directly onto the second surface 152 of the side elastomeric material 124 is more preferable than applying the second adhesive 164 to the opposing (i.e., second) coverstock layer 126. This is because the second adhesive 164 tends to penetrate through any residual processing agents or oils that may remain on the surface of the side elastomeric material 124. Such residual materials, if left to remain on the side elastomeric material 124, may weaken the adhesive bonds and thus the laminate structure 120 over time. For example, if these residual materials are left intact, the bonds used to form the laminate 120 may weaken during the time interval prior to consumer purchase of the product.

Peel values for the laminate 120 in the spiral adhesive areas are typically higher when the spirals 166 are applied directly to the side elastomeric material 124 than to the opposing (i.e., second) coverstock layer 126. Herein "peel value" refers to the amount of force required to separate the two layers of coverstock material, 122 and 126, from each other. Higher peel values typically equate to less chance of delamination in use.

A third adhesive 160 may also preferably be applied to the inner surface 142 of the first coverstock layer 122. Preferably, the third adhesive 160 is an elastomeric adhesive. In a manner similar to that described with reference to the second spiral adhesive application 166, the first adhesive 160 is preferably applied in a spiral spray pattern 162, thereby forming bond points 167a that are more discrete than would be formed by a linear spray application. Without being bound by theory, it is believed that most of the first adhesive 160 so sprayed aligns in the structural direction D.

Preferably, second and third adhesives 160 and 164 are the same elastomeric adhesive. A preferred adhesive for use in the second and third adhesive spiral sprays 162 and 166 is made by the Findley Adhesive Company under the designation H2120. Preferably, the add-on level for each of the second and third spiral sprays 162 and 166 is about 0.062 to about 0.186 $g/m^2$, more preferably about 0.124 $g/m^2$.

Figure 7:
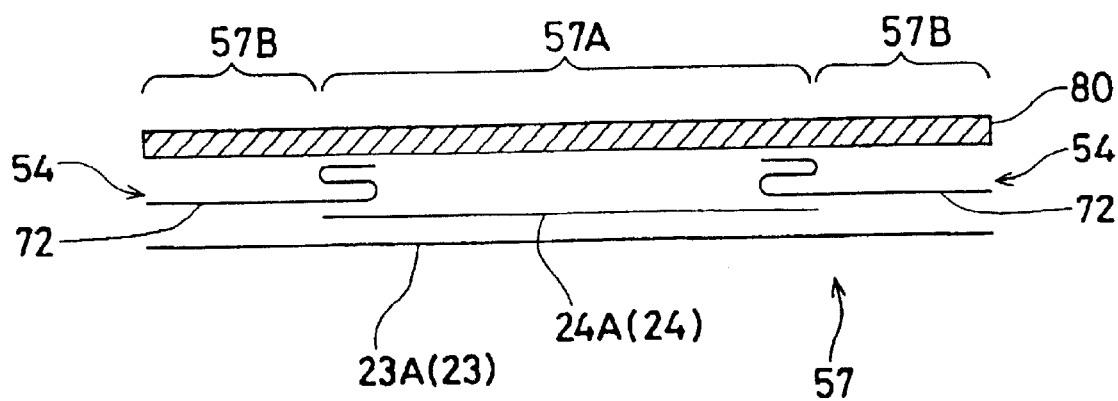
FIG. 7 is a cross-sectional view of a preferred embodiment taken along the section line 6—6 of FIG. 3.

Referring to FIGS. 1, the pull-on diaper 20 further has the continuous extensible waist feature 60. The continuous extensible waist feature 60 improved fit, ease of application and containment. The continuous extensible waist feature 60 is that portion or zone of the pull-on diaper 20 which is intended to be elastically extensible and contract to dynamically fit the wearer's waist. The continuous extensible waist feature 60 extends along the waistband panel 6 and 7. Preferably, the continuous extensible waist feature 60 comprises two separate elements; one continuous extensible waistband 57 positioned in the front region 26, and the other continuous extensible waistband 59 positioned in the back region 28, although other pull-on diapers can be constructed with a single continuous extensible waistband. Referring to FIG. 7 as well, the continuous extensible waistband 57 and 59 preferably comprises a waist elastic member 80 having the waist elastomeric material 200 (shown in FIG. 8) and an extended portion of at least one of the plurality of layers disposed associated with the absorbent core 25, such as the topsheet 24 and the backsheet 22 (although FIG. 7 depicts only the structures in the front region 26, preferably the structures in the back region 28 are the same or similar to those in the front region 26). Preferably the continuous extensible waistband 57 and 59 is elastically extensible in at least the lateral direction, more preferably both in the lateral and longitudinal directions. In a preferred embodiment, the waistband panel 6 and 7 is rendered extensible at least in the entire lateral length of the waistband panel 6 and 7 to form the continuous extensible waistband 57 and 59 by the waist elastic member 80. In the embodiment shown in FIG. 3, the waist elastic member 80 may extend into the seam panel 12 and 13 so that the continuous extensible waistband 57 and the continuous extensible waistband 59 are anchored each other at the seam 32, and the waist elastic material 80 in the front region 26 and the elastic material 80 in the back region 28 are anchored at the seam 32 (FIG. 7 also shows the waist elastic member 80 which extends into the seam panel 12 and 13, though the seam panel 12 and 13 is not shown in FIG. 7). The continuous extensible waistband 57 and 59 forms one continuous extensible waist feature 60 in an assembled configuration of the pull-on diaper 20 as shown in FIG. 1.

The continuous extensible waistband 57 and 59 may be formed by unitary elements of the pull-on diaper 20 (i.e., they are not separately manipulative elements secured to the pull-on diaper 20, but rather are formed from and are extended portions of one or more of the various layers of the pull-on diaper). In a preferred embodiment, each of the continuous extensible waistband 57 and 59 comprises a projected member of the chassis 41. Preferably, the continuous extensible waistband 57 and 59 comprises at least one unitary element or a continuous sheet material that forms a part of the chassis 41 and continuously extends into the continuous extensible waistband 57 and 59. Alternatively, the continuous extensible waistband 57 and 59 may be discrete members which do not have any unitary element that forms a part of the chassis 41. The continuous extensible waistband 57 and 59 may be formed by joining the discrete members to the waist portions of the chassis 41.

The continuous extensible waistband 57 and 59 comprises the waist elastic member 80 and an extended portion of at least one of the plurality of layers disposed associated with the absorbent core 25, such as the topsheet 24 and the backsheet 22. If an additional layer, such as the inner barrier cuff 54 or an additional liquid absorbing tissue layer, is added associated with the absorbent core 25, the additional layer may form a part of the continuous extensible waistband 57 and 59. In a preferred embodiment shown in FIG. 7, the side portion 57B of the continuous extensible waistband 57 comprises a lamination of an extended portion 72 of the inner barrier cuff 54, the end extended portion 23A of the nonwoven outer cover 23, and a side part of the waist elastic member 80. The central portion 57A of the extensible waistband 57 comprises a lamination of the end extended portion 24A of the topsheet 24, the end extended portion 23A of the nonwoven outer cover 23, and a center part of the waist elastic member 80 (although FIG. 7 depicts only the structures in the front region 26, preferably the structures in the back region 28 are the same or similar to those in the front region 26). However, in the embodiment, the inner barrier film 68 does not extend into the continuous extensible waistband 57. Alternatively, the inner barrier cuff 54, the topsheet 24 and/or the nonwoven outer cover 23 may not extend into the continuous extensible waistband 57. The extended portion 72 of the inner barrier cuff 54 also may not extend into the continuous extensible waistband 57. If both of the topsheet 24 and the nonwoven outer cover 23 do not extend into the continuous extensible waistband 57, the continuous extensible waistband 57 may comprise an extended portion of the inner barrier film 68 and the waist elastic member 80.

The waist elastic member 80 is superposed inside the innermost surface (body-facing surface) of the pull-on diaper 20. The waist elastic member 80 may be operatively joined to the extended portions 72 of the inner barrier cuffs 54, the end extended portion 23A of the nonwoven outer cover 23, and the end extended portion 24A of the topsheet 24. The waist elastic member 80 can be operatively joined thereto, by using either an intermittent bonding configuration or a substantially continuous bonding configuration. In a particularly preferred embodiment, the adhesive selected is applied in a spiral pattern (such as is shown in U.S. Pat. No 3,911,173 (Sprague, Jr.) and U.S. Pat. No. 4,842,666 (Werenicz)) at a basis weight of about 0.116 g/m². The spirals have a width of about 1.9 cm (0.75 in) and either are positioned just next to each other or overlap slightly (less than 2 mm). The adhesive is preferably an adhesive such as is available from Findley Adhesives under the designation H2120. Alternatively, the waist elastic member and any other components of the stretch laminates may be intermittently or continuously bonded to one another using heat bonding, pressure bonding, ultrasonic bonding, dynamic mechanical bonding, or any other method as is known in the art.

The entire unstrained length of the waist elastic member 80 is preferably prestrained in the lateral direction before operatively joined to the extended portions 72 of the left and right inner barrier cuffs 54, the end extended portion 24A of the topsheet 24, and the end extended portion 23A of the nonwoven outer cover 23. The entire unstrained length of the waist elastic member 80 is prestrained in the lateral direction up to at least the original length of the waistband panel 6 and 7 of the chassis 41. The entire unstrained length of the waist elastic member 80 may be further prestrained to extend into a part of the seam panel 12 and 13. In the embodiment, the waistband panel 6 and 7 of the chassis 41 comprises the extended portions 72 of the left and right inner barrier cuffs 54, the end extended portion 24A of the topsheet 24, and the end extended portion 23A of the nonwoven outer cover 23. Herein "original length" refers to the length of a single material or a composite material before being rendered elastically extensible and before being permanently mechanically stretched. Herein "prestrained entire length" refers to the entire length of an elastic material under a condition where a part of or the entire length of the elastic material is prestrained in the lateral direction. In the embodiment, the original length of the waistband panel 6 and 7 is generally the same as the combined length of the extended portions 72 of the left and right inner barrier cuffs 54 and the end extended portion 24A of the topsheet 24 under an assembled configuration before the waist elastic member 80 is joined thereto. The original length of the waistband panel 6 and 7 is also generally the same as the length of the end extended portion 23A of the nonwoven outer cover 23 before the waist elastic member 80 is joined thereto. The waist elastic member 80 is preferably prestrained in range of from 20 to 100% of its unstrained (i.e. untensioned) length. More preferably, the waist elastic member 80 may be prestrained in range of from 40 to 80%. After the prestrained waist elastic member 80 is joined, the waist elastic member 80 is then allowed to return to their substantially untensioned condition with the other components, such as the extended portions 72 of the inner barrier cuffs 54, the end extended portion 24A of the topsheet 24, and the end extended portion 23A of the nonwoven outer cover 23, joined to the waist elastic member 80. Thus the continuous extensible waistband 57 and 59 is formed that is extensible, from the untensioned length of the waist elastic member 80 at least to the original length of the waistband panel 6 and 7 of the chassis 41.

Alternatively, only a part of the waist elastic member 80 may be prestrained before operatively joined to the extended portion of at least one of the plurality of layers, such that the prestrained entire length of the waist elastic member 80 in a condition where a part of the waist elastic member 80 is prestrained is generally the same as the original length of the waistband panel 6 and 7 of the chassis 41. Preferably, only a part of the waist elastic material 80, which extends along the lateral width X (shown in FIG. 3) of the absorbent core 25 adjacent to the waist elastic material 80, may be prestrained.

Examples of extensible materials are disclosed in U.S. Pat. No. 2,075,189 issued to Galligan on Mar. 30, 1937; U.S. Pat. No 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No 4,834,741 issued to Sabee on May 30, 1989; and U.S. Pat. No. 5,151,092 issued to Buell et al., on Sep. 29, 1992.

The continuous extensible waistband 57 and 59 is formed to be extensible, from the untensioned length of the waist elastic member 80 at least up to the original length of the waistband panel 6 and 7 of the chassis 41. However, the waist elastic member 80 is usually joined to the extended portion of at least one of the plurality of layers disposed associated with the absorbent core 25, such as the topsheet 24 and the backsheet 22 which are substantially non-elastic. Therefore, the waist elastic member 80 can extend only between the untensioned length of the waist elastic member 80 and the original length of the waistband panel 6 and 7 of the chassis 41, and can not extend beyond the original length of the waistband panel 6 and 7 of the chassis 41. This restricts the upper limit of the extension range of the continuous extensible waistband 57 and 59 (i.e., continuous extensible waist feature 60), even if the waist elastomeric material 80 itself is capable of extending beyond the original length of the waistband panel 6 and 7 of the chassis 41 or the prestrained entire length of the waist elastomeric material 80. This restriction in the upper limit of the extension range does not allow enough extensibility for the continuous extensible waistband 57 and 59. Therefore, when the pull-on diaper 20 is extended for application to the wearer, the pull-on diaper 20 may not provide enough size of waist opening or the applicator must apply much high force to the pull-on diaper 20 to seek extensibility from other extensible materials in the pull-on diaper 20 to obtain enough size of waist opening. This may cause difficulty in applying the pull-on diaper to the wearer.

Therefore, the continuous extensible waistband 57 and 59 is rendered elastically extensible to provide greater range of extensibility (i.e., extension range) beyond the original length of the waistband panel 6 and 7 of the chassis 41 or the prestrained entire length of the waist elastic member 80. Namely, after the waist elastic member 80 is operatively joined under a prestrained (tensioned) condition to the inner barrier cuff 54, the topsheet 24 and the nonwoven outer cover 23 and before returning to their substantially untensioned condition, at least a portion of, preferably the entire of the resultant composite stretch laminate (i.e., continuous extensible waistband 57 and 59) is then subjected to mechanical stretching sufficient to permanently elongate the non-elastic components which are the extended portions 72 of the left and right inner barrier cuffs 54, the end extended portion 24A of the topsheet 24, the end extended portion 23A of the nonwoven outer cover 23, and the coverstock layers (if any) constituting a part of the waist elastic member 80. The composite stretch laminate is then allowed to return to its substantially untensioned condition. Therefore, the waist elastic member 80 is extensible from the untensioned length beyond the original length of the waistband panel 6 and 7 of the chassis 41 at least up to the permanently elongated length of the non-elastic components. This provides wider extension range for the continuous extensible waistband 57 and 59, thereby providing a benefit of ease of application. Alternatively the waist elastic member 80 may be joined to the inner barrier cuffs 54, the topsheet 24 and the nonwoven outer cover 23 in a substantially untensioned (zero strain) condition so as to form a "zero strain" stretch laminate. Preferred apparatus and methods are disclosed in U.S. Pat. No 5,167,897 issued to Weber et al. on Dec. 1, 1992; U.S. Pat. No 5,156,793 issued to Buell et al. on Oct. 20, 1990; U.S. Pat. No. 5,143,679 issued to Weber et al. on Sep. 1, 1992 and European Patent Application No. 98108290.2 titled "METHOD AND APPARATUS FOR ACTIVATING A MOVING WEB" filed on May 7, 1998 (Christoph J. Schmitz et al.).

The waist elastic member 80 comprises the waist elastomeric material 200 which can use the same material/structure as the side elastomeric material 124. Alternatively, the waist elastomeric material 200 may use material/structure different from the side elastomeric material 124. The waist elastic member 80 may further include one of, or both of a first coverstock layer 202 and a second coverstock layer 204. The structure of the waist elastic member 80 may be the same or similar to that of the side elastic member 70. The structure, materials and/or properties of the coverstock layers 202 and 204 may be the same or similar to those of the coverstock layers 122 and 126, or may be different from those. Further, the method to join the waist elastomeric material 200 to the coverstock layers 202 and 204 may be the same or similar to the method of those described for the ear panel member 70 above, or may be different from those. In a preferred embodiment, the waist elastic member 80 comprises the waist elastomeric material 200 and one layer of the coverstock layer 202 or 204. In such a case, the waist elastomeric material 200 is disposed facing the inner barrier cuffs 54 and the topsheet 27, and the coverstock layer 202 or 204 is disposed so as to face and contact the wearer's body such that the wearer's skin is not directly pressed by the waist elastomeric material 200 thereby reducing the incidence of red marking on the skin.

Figure 12:
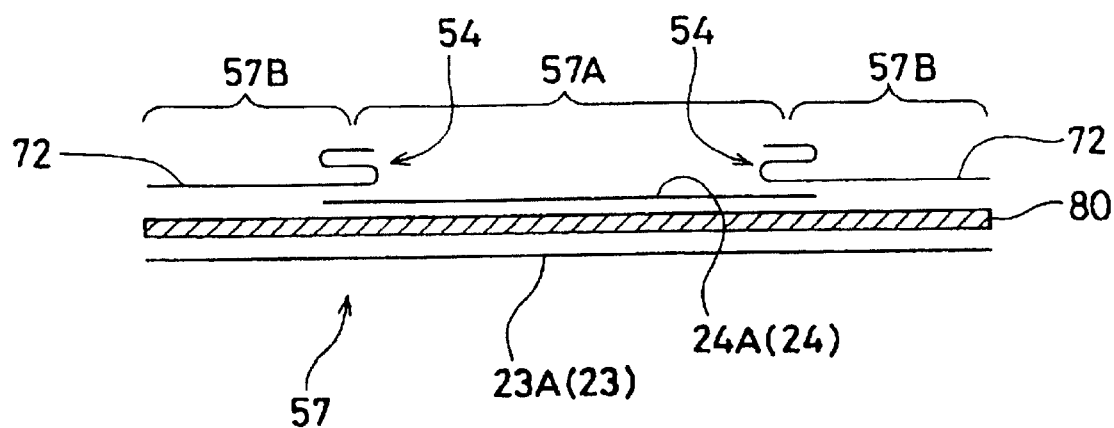
FIG. 12 is a cross-sectional view of an alternative embodiment taken along the section line 6—6 of FIG. 3.

FIG. 12 shows another preferred embodiment of the continuous extensible waistband 57 and 59. In this embodiment, the waist elastic member 80 is superposed inside the nonwoven outer cover 23. Preferably, in the side portions 57B of the continuous extensible waistband 57, the waist elastic member 80 is interposed between the extended portions 72 of the inner barrier cuffs 54 and the end extended portion 23A of the nonwoven outer cover 23. In the central portion 57A, the waist elastic member 80 is interposed between the end extended portion 24A of the topsheet 24 and the end extended portion 23A of the nonwoven outer cover 23. The waist elastic member 80 may be operatively joined to the extended portions 72 of the inner barrier cuffs 54, the end extended portion 23A of the nonwoven outer cover 23, and the end extended portion 24A of the topsheet 24. In one embodiment, the waist elastic member 80 may comprise the waist elastomeric material 200 and one layer of the coverstock layer 202 or 204. In one case, the waist elastomeric material 200 is disposed facing the inner barrier cuffs 54 and the topsheet 27, and the coverstock layer 202 or 204 is disposed facing the nonwoven outer cover 23. This disposition of the coverstock layer tends to inhibit the waist elastomeric material 200 is seen through from the outside because one layer (coverstock layer) is added to interpose between the waist elastomeric material 200 and the nonwoven outer cover 23. In another case, the waist elastomeric material 200 is disposed facing the nonwoven outer cover 23, and the coverstock layer 202 or 204 is disposed facing the inner barrier cuffs 54 and the topsheet 27. This disposition of the coverstock layer tends to reduce the incidence of red marking on the skin because one layer (coverstock layer) is added to interpose between the waist elastomeric material 200 and the skin of the wearer. In both cases, because one of the coverstock layers is eliminated (compared with two layers of the coverstock layers), bulkiness in the continuous extensible waistband 57 reduces. Further, breathability at the continuous extensible waistband 57 enhances because of less material therein. In addition, the continuous extensible waistband 57 becomes to have more available extensibility. The continuous extensible waistband 57 is formed by the waist elastic member 80 comprising the waist elastomeric material 200 which is prestrained and then returned to the original untensioned condition in a preferred embodiment. When the waist elastomeric material 200 returns to its original untensioned condition, the other components joined to the waist elastomeric material 200 tends to inhibit the waist elastomeric material 200 to return its original untensioned length. Therefore, the waist elastomeric material 200 can not utilize the whole extensibility. However, in the embodiment described above, since bulkiness in the continuous extensible waistband 57 reduces, the waist elastomeric material 200 can return as close as its original untensioned length. Therefore, the waist elastomeric material 200 becomes to have more available extensibility.

Alternatively, the waist elastic member 80 may comprise one layer of the waist elastomeric material 200 without any coverstock layers. In the side portions 57B of the extensible waistband 57, the waist elastomeric material 200 is interposed and joined directly between the extended portions 72 of the inner barrier cuffs 72 and the end extended portion 23A of the nonwoven outer cover 23. In the central portion 57A, the waist elastomeric material 200 is interposed and joined directly between the end extended portion 24A of the topsheet 24 and the nonwoven outer cover 23. This structure is also useful to reduce bulkiness, to enhance breathability, and to have more available extensibility, in the extensible waistband 57.

The side elastic member 70 and the waist elastic member 80 consist of separate elements and both members 70 and 80 are preferably disposed not to overlap to each other in the longitudinal direction. However, both members 70 and 80 are preferably disposed without a substantial gap in between such that the members 70 and 80 form a composite elastomeric network in the extensible ears 46 and 48. Herein "composite elastomeric network" refers to a zone or area where two or more separate elastomeric materials substantially continue with no gap between the elastomeric materials or with a predetermined interval, thereby exhibiting a behavior of extensibility like a single elastomeric material. Preferably, both members 70 and 80 are disposed with no gap. Therefore, it is perceived that the extensible ear 46 and 48 and the side portion 57B and 59B of the continuous extensible waistband 57 and 59 comprise a continuous single elastomeric material between the waist opening 36 and the leg openings in an assembled configuration of the pull-on diaper 20. The side elastic member 70 and the waist elastic member 80 consist of separate elements, therefore the side elastomeric material 124 and the waist elastomeric material 200 also consist of separate elements. The separated structure allows the design of the side elastomeric material 124 and the waist elastomeric material 200 using different materials in each component, so this allows different properties of extensibility such as force versus extension curve for different parts of the pull-on diaper 20. The separated structure also allows use of the side elastomeric material 124 and the waist elastomeric material 200 in different conditions, such as in a prestrained (tensioned) condition or untensioned condition. This allows differentiation of the force required to extend different parts of the pull-on diaper 20 up to the same length or equalize force required to extend different parts up to the different length, thereby adjusting the pressure applied to the skin of the wearer. For example, the pull-on diaper 20 may have a waist elastomeric material 200 provided with high extensibility at low force such that the continuous extensible waist feature 60 is extended easily by low force applied by the applicator for ease of application of the pull-on diaper 20 while the pull-on diaper 20 may have a side elastomeric material 124 generating force required for sustained fit at the extensible ear 46 and 48, but the force may not give red marking to the skin. In one embodiment, the continuous extensible waist feature 60 comprising the waist elastomeric material 200 is designed to have extensibility of at least 100% while the extensible ear 46 and 48 comprising the side elastomeric material 124 is designed to have force between 40 g/inch and 130 g/inch when the extensible ear 46 and 48 is extended up to 50% (more concretely, at SCRF50%).

Both the side elastic member 70 and the waist elastic member 80 are disposed not to overlap to each other in the longitudinal direction, therefore, the side elastomeric material 124 and the waist elastomeric material 200 also do not overlap. Because the side elastic member 70 and the waist elastic member 80 are not structurally overlapped, each member 70 and 80 comprises a single material of extensibility, therefore it has substantially homogeneous property of extensibility. This allows the applicator to extend the pull-on diaper 20 smoothly without feeling the change of force applied during extending for application of the pull-on diaper.

The seams 32 each join the seam panels 12 and 13, thereby joining the corresponding portions of the extensible ears 46 and 48, and thereby forming two leg openings 34 and one waist opening 36. The front and back extensible ears 46 and 48 are seamed, preferably, along the outer side edges 46D and 48D, in an overlapped manner to make an overlapped seam structure. Alternatively, the front and back extensible ears 46 and 48 can be seamed in a butt seam manner (not shown in Figs.). The bonding of the seams 32 can be performed by any suitable means known in the art appropriate for the specific materials employed in the front and back extensible ears 46 and 48. Thus, sonic sealing, heat sealing, pressure bonding, adhesive or cohesive bonding, sewing, autogeneous bonding, and the like may be appropriate techniques. Preferably, the seam panels 12 and 13 are joined by a predetermined pattern of heat/pressure or ultrasonic welds which withstands the forces and stresses generated on the pull-on diaper 20 during wear. The seams 32 also connect the continuous extensible waistbands 57 and 59 to form the continuous extensible waist feature 60 about the waist opening 36. When the side elastic member 70 and the waist elastic member 80 extend into the seam panel 12 and 13, the seams 32 anchor the side elastic member 70 in the front region 26 to the side elastic member 70 in the back region 28 and anchor the waist elastic member 80 in the front region 26 to the waist elastic member 80 in the back region 28. Examples of seams are disclosed in U.S. Pat. No 5,569,234 issued to Buell, et al. on Oct. 29, 1996, U.S. Pat. No 5,607,537 issued to Johnson et al. on Mar. 4, 1997, U.S. Pat. No 5,662,638 issued to Johnson et al. on Sep. 2, 1997, and U.S. Pat. No 5,685,874 issued to Buell et al. on Nov. 11, 1997. Preferable seams are disclosed in European Patent Application No. 96118654.1 titled "Thermal Joining of Webs" filed on Nov. 21, 1996 (Christoph J. Schmitz).

Figure 13:
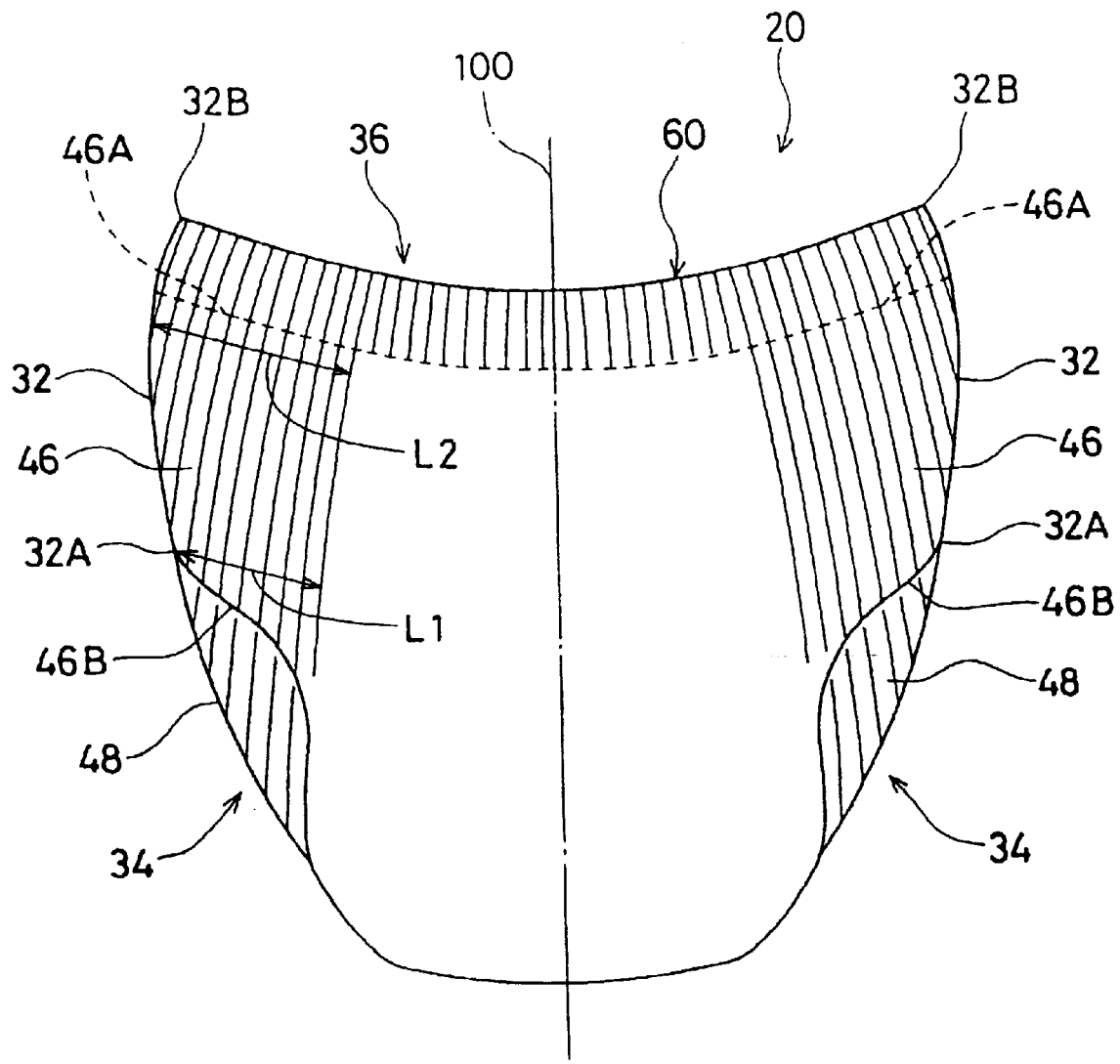
FIG. 13 is a front view of the embodiment shown in FIG. 1.
Figure 14:
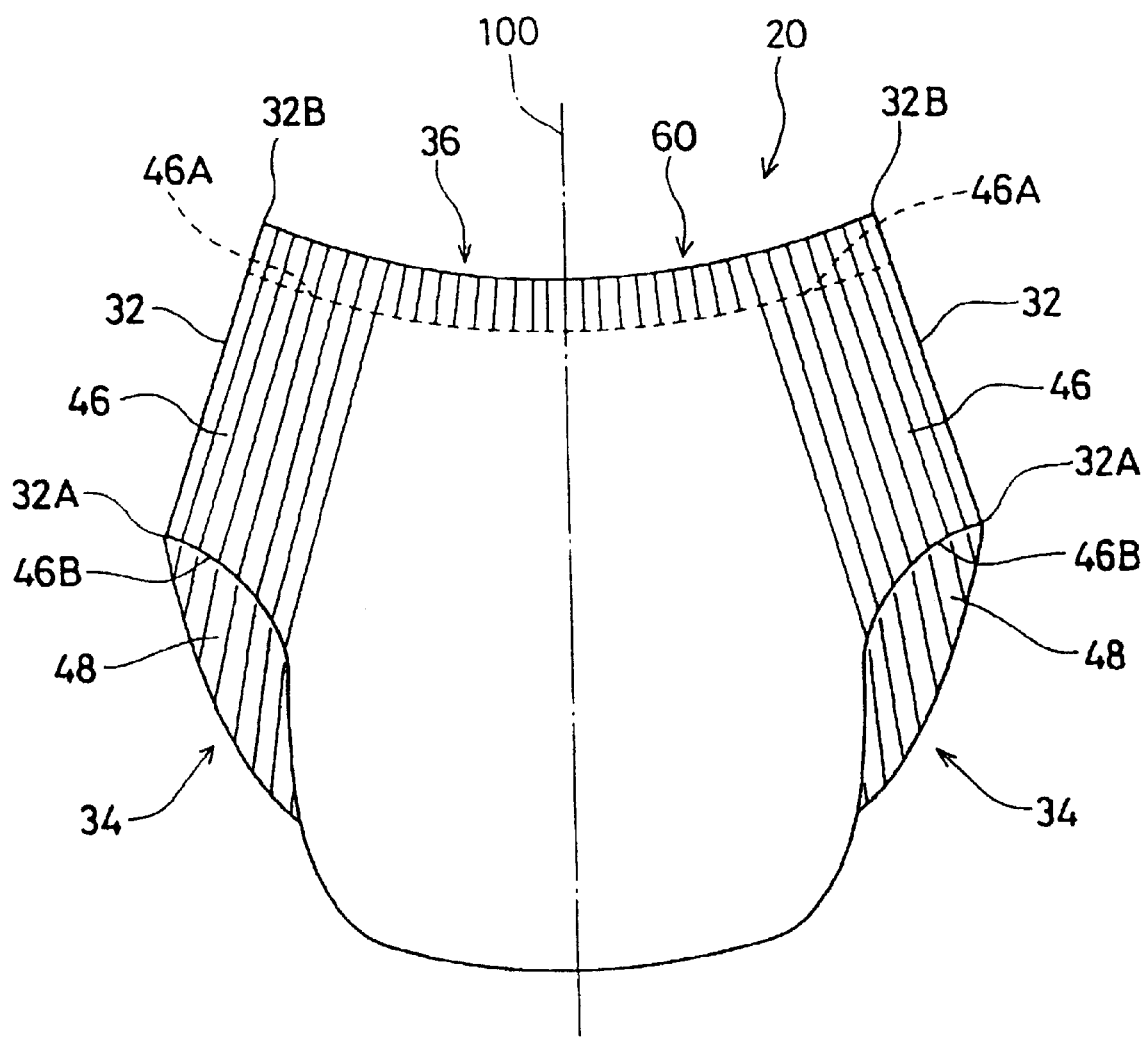
FIG. 14 is a front view of an alternative embodiment of the disposable pull-on garment.

In a preferred embodiment, the outer side edge 46D and 48D is non-parallel to the inner side edge 46C and 48C and is non parallel to the longitudinal center line 100. The outer side edge 46D and 48D projects laterally outwardly proximate the higher end edge 46A and 48A. The extensible ear 46 and 48 has a lateral width L2 between the inner side edge 46C and 48C and the outer side edge 46D and 48D proximate the higher end edge 46A and 48A greater than a lateral width L1 between the inner side edge 46C and 4BC and the outer side edge 46D and 48D proximate the lower end edge 46B and 48B. Therefore, the available elastomeric material quantity in the lateral direction of the extensible ear 46 and 48 is greater proximate the higher end edge 46A and 48A than proximate the lower end edge 46B and 48B. The extensibility proximate the higher end edge 46A and 48A is enhanced. In addition, because both extensible ear 46 and extensible ear 48 have greater lateral width (i.e., available elastomeric material quantity) proximate the higher end edge 46A and 48A, lateral width (i.e., available elastomeric material quantity) further becomes greater proximate the higher end edge 46A and 48A by combining the extensible ear 46 and the extensible ear 48. Because of the configuration being greater width proximate the higher end edge 46A and 48A, the pull-on diaper has more elastomeric material quantity available about the waist openings. Therefore, the pull-on diaper does not give too high pressure to the skin causing the negative skin incidence about the waist opening while maintaining a sustained fit about the leg openings. Further, it provides a benefit of ease of application. In a configuration where the extensible ear 46 and the extensible ear 48 are joined, the seam 32 is non-parallel to the longitudinal center line 100 as shown in FIG. 13 such that the seam 32 projects laterally outwardly proximate the higher portion 32B of the seam 32. In FIG. 13, the waist elastic member 80 is joined to the waistband panel 6 and 7 of the chassis 41 in a tensioned (prestrained) condition and allowed to return to the substantially untensioned condition while the side elastic member 70 is joined to the extensible ear 46 and 48 in an untensioned condition. Therefore, the circumference along the continuous extensible waist feature 60 is a little contracted. If the waist elastomeric material 200 is further prestrained, the circumference along the continuous extensible waist feature 60 becomes smaller than the circumference of the pull-on diaper 20 through a portion of the extensible ear 46 and 48 as shown in FIG. 14. However, because of the original configuration of the extensible ear 46 and 48 having greater lateral width proximate the higher end edge 46A and 48A, the pull-on diaper 20 shown in FIG. 14 still has greater elastomeric material quantity proximate the higher end edge 46A and 48A. Herein "circumferential direction" refers to a direction along the waist opening in an assembled configuration of the pull-on diaper. Herein "circumference" refers to a length of the pull-diaper along the circumferential direction.

The continuous belt zone 38 is formed by the front and back extensible ears 46 and 48, a part of the chassis 41, and the continuous extensible waist feature 60 as shown in FIG. 1. The continuous belt zone is that portion or a belt-like zone of the pull-on diaper which is extensible such that the circumference of the continuous belt zone is extended for application of the pull-on diaper 20. When the pull-on diaper 20 is applied to the wearer, the pull-on diaper 20 must be extended to secure wider waist opening and wider leg opening for ease of application of the pull-on diaper 20. The continuous belt zone 38 is that portion capable of being extended. The continuous belt zone 38 is, in an assembled configuration shown in FIG. 1, encompassed by the waist edge 151 and 155 of the pull-on diaper 20, the leg edge 153 and 156, the lateral edge 159 of the crotch region 30 in the front region 26 and the back region 28. The continuous belt zone 38 has the least height typically at the ear panels. In the embodiment shown in FIG. 1, the least height of the continuous belt zone 38 is measured along the seams 32. The continuous belt zone 38 also has a continuous lowermost line 35 which is not interrupted by the leg openings 34, but is the closest to the leg openings 34. The continuous belt zone 38 has two portions; a continuous waist belt zone 37 in which the continuous extensible waist feature 60 extends, and a continuous lower belt zone 39 in which the extensible ears 46 and 48 and a part of the chassis 41 extend. In a preferred embodiment, the continuous waist belt zone 37 conforms with the continuous extensible waist feature 60.

In one preferred embodiment where the pull-on diaper shown in FIG. 3 becomes an assembled configuration as shown in FIG. 1, the initial circumference of the continuous belt zone 38 along the waist end edge 151 and 155 may be from 220 mm to 520 mm in an untensioned condition, preferably from 270 mm to 420 mm. The circumference of the continuous belt zone 38 along the waist end edge 151 and 155 extends up to at least 650 mm, preferably at least 700 mm, more preferably at least 750 mm (extended circumference). The circumference of the continuous belt zone 38 along the line 35 may be from 300 mm to 530 mm, preferably from 380 mm to 480 mm. The least height of the continuous belt zone 38 measured along the seams 32 may be from 50 mm to 150 mm, preferably from 80 mm to 120 mm. The height of the continuous waist belt zone 37 (i.e., continuous extensible waist feature 60) may be from 5 mm to 40 mm, preferably from 15 mm to 30 mm. The combined lateral length of the extensible ears 46 and 48 in one side of the pull-on diaper 20 along the line 35 is from 50 mm to 120 mm, preferably from 60 mm to 100 mm.

The pull-on diaper having the configuration shown in FIG. 3, when it becomes an assembled configuration, lowers the pressure to the skin of the wearer locally especially about the waist opening 34 because the extensible ear 46 and 48 has greater lateral width (available elastomeric material quantity in a lateral direction) proximate the higher end edge 46A and 48A. If necessary, the waist elastomeric material 200 may use a material having lower SCRF50% force to further lower the pressure about the waist opening 36. However, lowering the SCRF50% force about the waist opening 36 may result in losing sustained fit for the whole pull-on diaper. Therefore, raising the pressure about the leg openings 34 may be necessary to achieve sustained fit for the whole pull-on diaper. This may be achieved by prestraining only the side elastomeric material 124 before joining to the ear panel 10 and 11. In addition, the side elastomeric material 124 may use a material having a higher SCRF50% force to further raise the pressure about the leg openings 34. These combinations of force distributions allow the pull-on diaper to achieve a sustained fit about the leg openings with less incidence of red marking on the skin about the waist opening. Alternatively, the pull-on diaper having a configuration shown in FIG. 3, when it becomes an assembled configuration, may provide a sustained fit about the waist opening and less incidence of red marking on the skin about the leg openings. This can be achieved, for example, using a material having lower SCRF50% force for the side elastomeric material 124 to lower the pressure about the leg openings 34. The waist elastomeric material 200 may use a material having a higher SCRF50% force. Further, the waist elastomeric material 200 may be prestrained before joining to the waistband panel 6 and 7.

The continuous belt zone 38 contributes to dynamically create fit force in the pull-on diaper 20 when positioned on the wearer, to maintain the pull-on diaper 20 on the wearer. Although higher fit force generated by the continuous belt zone 38 is preferable for sustained fit for the pull-on diaper, the continuous belt zone 38 generating the higher fit force causes difficulty in applying the pull-on diaper to the wearer because the applicator of the pull-on diaper must apply higher force to the pull-on diaper to extend the continuous belt zone 38 such that the wider waist opening and wider leg openings are secured. Because the continuous belt zone 38 comprises the side elastomeric material 124 and the waist elastomeric material 200, both elastomeric materials must be extended during the process of pulling on the pull-on diaper. Therefore, the property of extensibility of the continuous belt zone 38 including the side and waist elastomeric materials are more important than those of a solo continuous extensible waist feature 60 and/or those of a solo extensible ear 46 and 48, though the property of extensibility of a solo continuous extensible waist feature 60 and/or a solo extensible ear 46 and 48 are still important. Prior art such as U.S. Pat. No. 5,601,547 published on Feb. 11, 1997 to Kato, et al. discloses a waist elastic system with improved modulus of elasticity for a child's training pant providing a more comfortable fit and improved ease of use. However, this publication is directed to only improvement of the waist elastic system.

The continuous belt zone 38 is extensible in the extension range from an initial extension (i.e., 0%). The extension is calculated from the equation: ((extended circumference−initial circumference)/initial circumference)×100 and expressed in the unit of % (percent). The initial circumference of the continuous belt zone 38 is the circumference under an untensioned condition of the continuous belt zone 38. The extended circumference is the circumference under an extended condition of the continuous belt zone 38. The wider extension range allows to secure the wider waist opening and the wider leg openings for application of the pull-on diaper 20. The wider extended circumference allows to secure the wider space between the extended pull-on diaper and the body of the wearer for application of the pull-on diaper 20. The circumference of the continuous belt zone 38 is the circumference measured along the waist border of the continuous belt zone 38 (i.e., the waist edges 151 and 155 of the continuous extensible waist feature 60).

In order to provide a benefit of ease of application of the pull-on diaper (i.e., wider waist opening and wider leg openings), the initial circumference of the continuous belt zone 38 of the pull-on diaper may be between about 220 mm and about 500 mm, and the extended circumference of the continuous belt zone 38 of the pull-on diaper is at least about 650 mm. More specifically, the initial circumference of the continuous belt zone 38 of the pull-on diaper designed to fit toddlers weighing from about 7 kgs to about 10 kgs is between about 220 mm and about 460 mm, preferably about 250 mm and about 360 mm. The initial circumference of the continuous belt zone 38 of thei pull-on diaper designed to fit toddlers weighing from about 9 kgs to about 14 kgs is between about 240 mm and about 480 mm, preferably about 270 mm and about 380 mm. The initial circumference of the continuous belt zone 38 of the pull-on diaper designed to fit toddlers weighing about 13 kgs or above is between about 260 mm and about 500 mm, preferably about 290 mm and about 400 mm. The extended circumference of the continuous belt zone 38 of the pull-on diaper designed to fit toddlers weighing from about 7 kgs to about 10 kgs is at least about 650 mm, preferably about 700 mm. The extended circumference of the continuous belt zone 38 of the pull-on diaper designed to fit toddlers weighing from about 9 kgs to about 14 kgs is at least about 700 mm, preferably about 750 mm. The extended circumference of the continuous belt zone 38 of the pull-on diaper designed to fit toddlers weighing about 13 kgs or above is at least about 750 mm, preferably about 800 mm. The pull-on diaper has the extension range up to at least the extension of about 125%, preferably about 135%, preferably at least about 150%.

The continuous belt zone 38 also has a force versus extension curve in the extension range and a modulus of extensibility in the extension range. The force versus extension curve represents a relationship of a force required to extend the continuous belt zone 38 and an extension of the continuous belt zone 38. The modulus of extensibility represents a rate of force change to extension change and is expressed in the unit of g/%extension (grams/percent extension). The modulus of extensibility is obtained based on the force versus extension curve. The higher modulus of extensibility means higher rate of force change to extend the continuous belt zone 38. When modulus of extensibility becomes dramatically high, the applicator recognizes that part as a limitation of extension. Conversely, the lower modulus of extensibility means lower rate of force change to extend the continuous belt zone 38. This allows the applicator to extend the continuous belt zone 38 without adding higher force, and the applicator may not recognize the limitation of extension. Therefore, it is preferable the continuous belt zone 38 has a lower modulus of extensibility at the extended circumference for application of the pull-on diaper. In addition, the lower force to extend the pull-on diaper up to the extended circumference for application of the pull-on diaper is preferable.

In order to provide a benefit of ease of application of the pull-on diaper (i.e., lower force to obtain the extension for application of the pull-on diaper and lower modulus of extensibility at the extension for application of the pull-on diaper), the modulus of extensibility at the extension of 125% is not greater than about 150 g/%extension, preferably not greater than about 120 g/%extension, more preferably not greater than about 100 g/%extension. The modulus of extensibility in the extension range up to the extension of 125% is preferably not greater than about 150 g/%extension, more preferably not greater than about 120 g/%extension. The modulus of extensibility at the extension of 135% is not greater than about 200 g/%extension, preferably not greater than about 175 g/%extension, more preferably not greater than about 150 g/%extension. The modulus of extensibility in the extension range up to the extension of 135% is preferably not greater than about 200 g/%extension, more preferably not greater than about 175 g/%extension. The modulus of extensibility at the extension of 150% is preferably not greater than about 300 g/%extension, more preferably not greater than about 250 g/%extension. The force to obtain the extension of 125% is preferably not greater than about 5,000 g, more preferably not greater than about 4,500 g. The force to obtain the extension of 135% is preferably not greater than about 6,000 g, more preferably not greater than about 5,500 g. The force to obtain the extension of 150% is preferably not greater than about 9,000 g, more preferably not greater than about 8,000 g.

Figure 15:
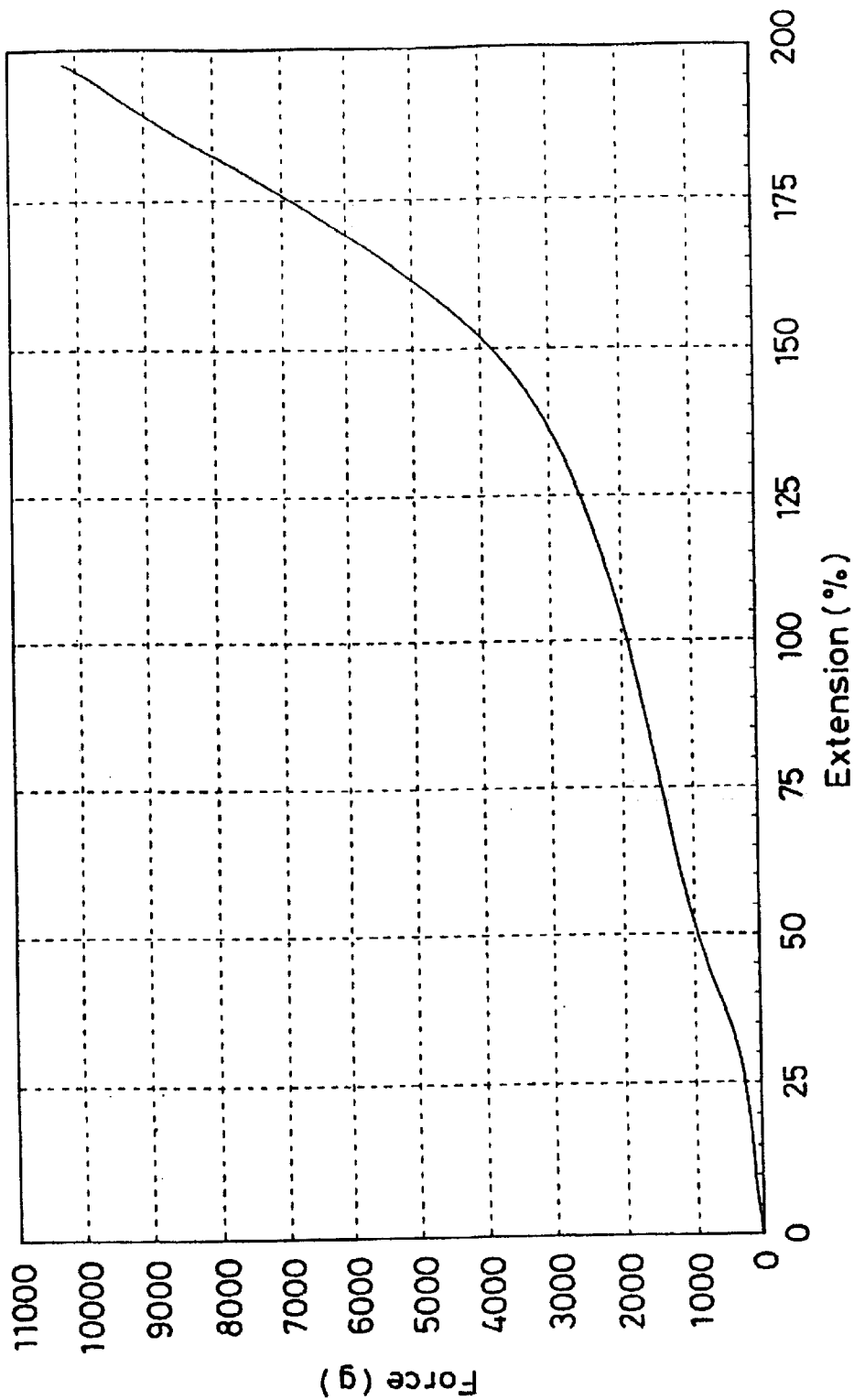
FIG. 15 illustrates force versus extension curve of the continuous belt zone of the disposable pull-on garments of the present invention.
Figure 16:
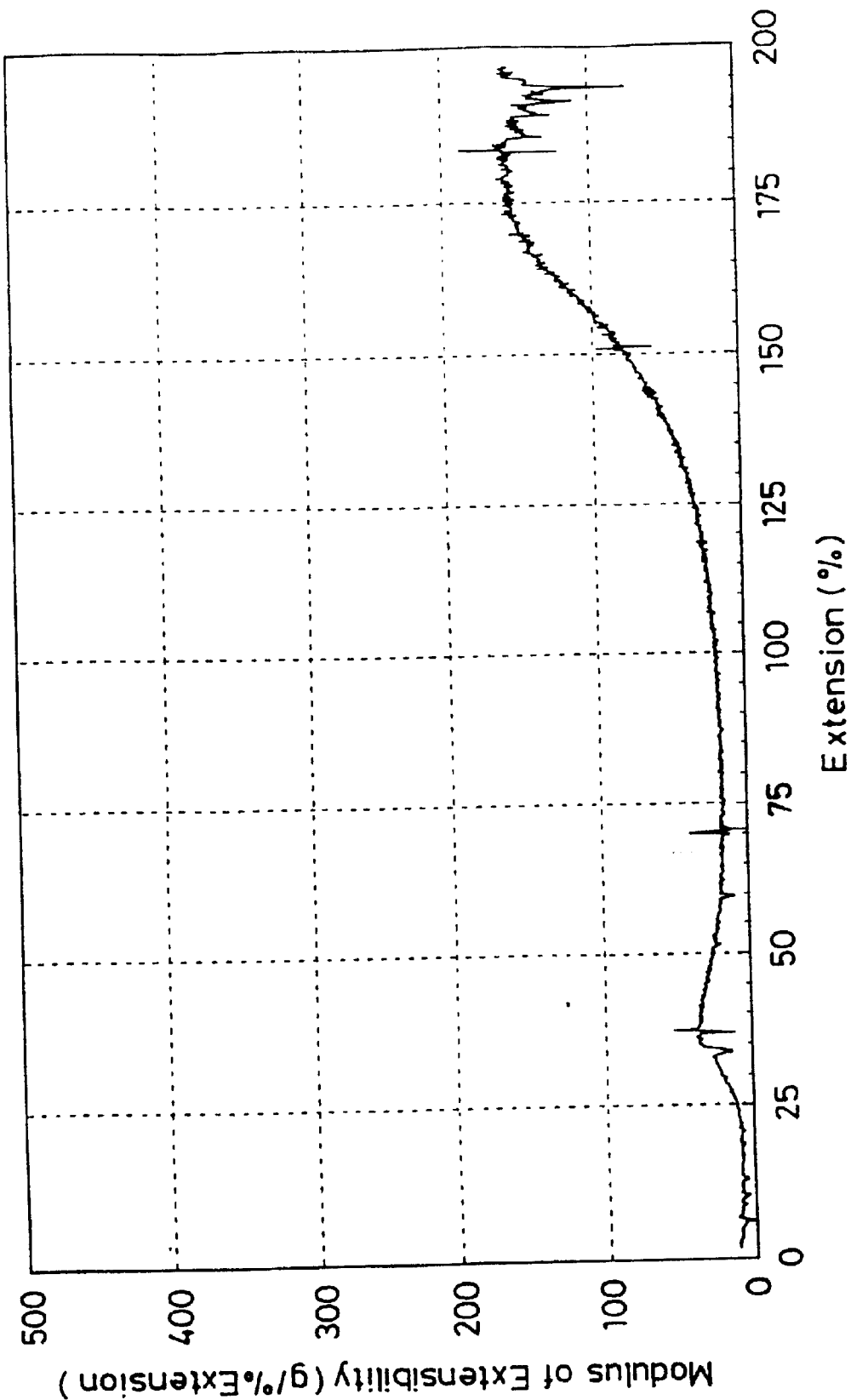
FIG. 16 illustrates modulus of extensibility versus extension curve obtained from the force versus extension curve shown in FIG. 15.
Figure 17:
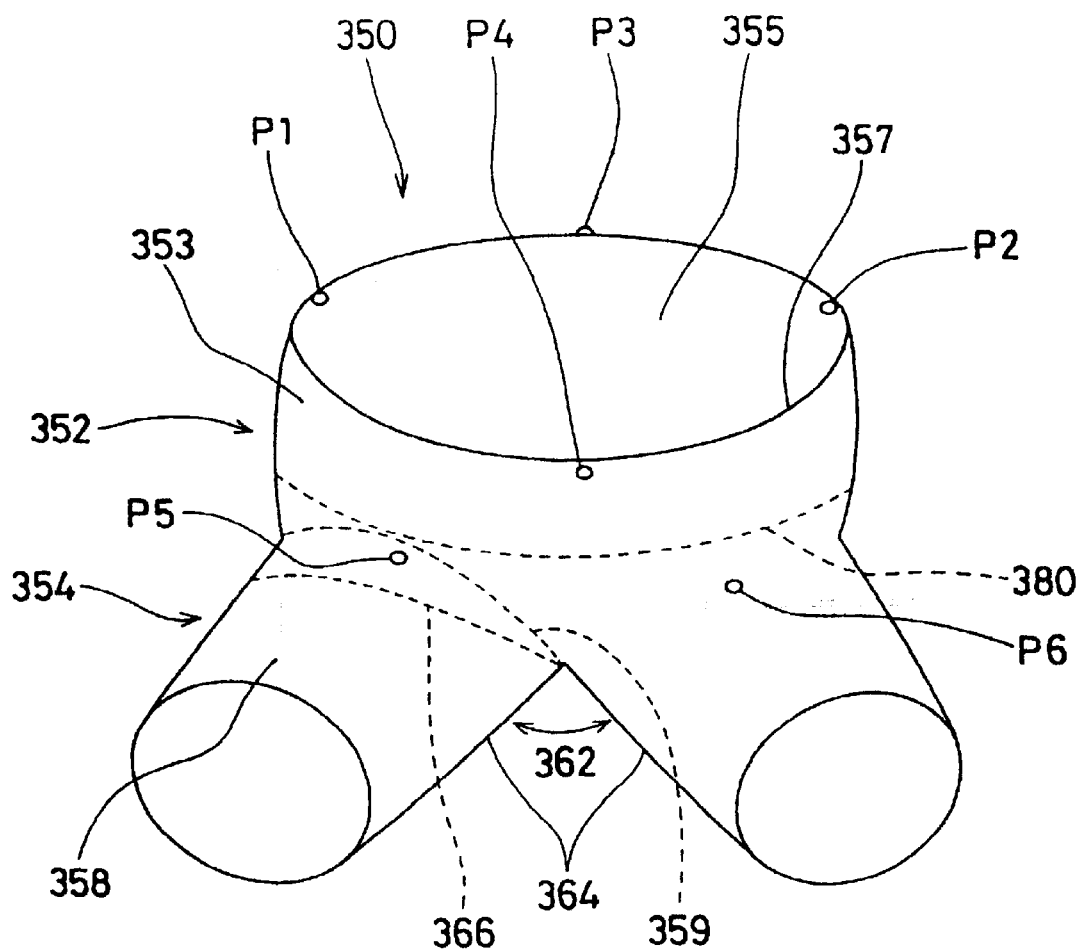
FIG. 17 is a perspective view of the standard mannequin used to measure skin contact pressure.
Figure 18:
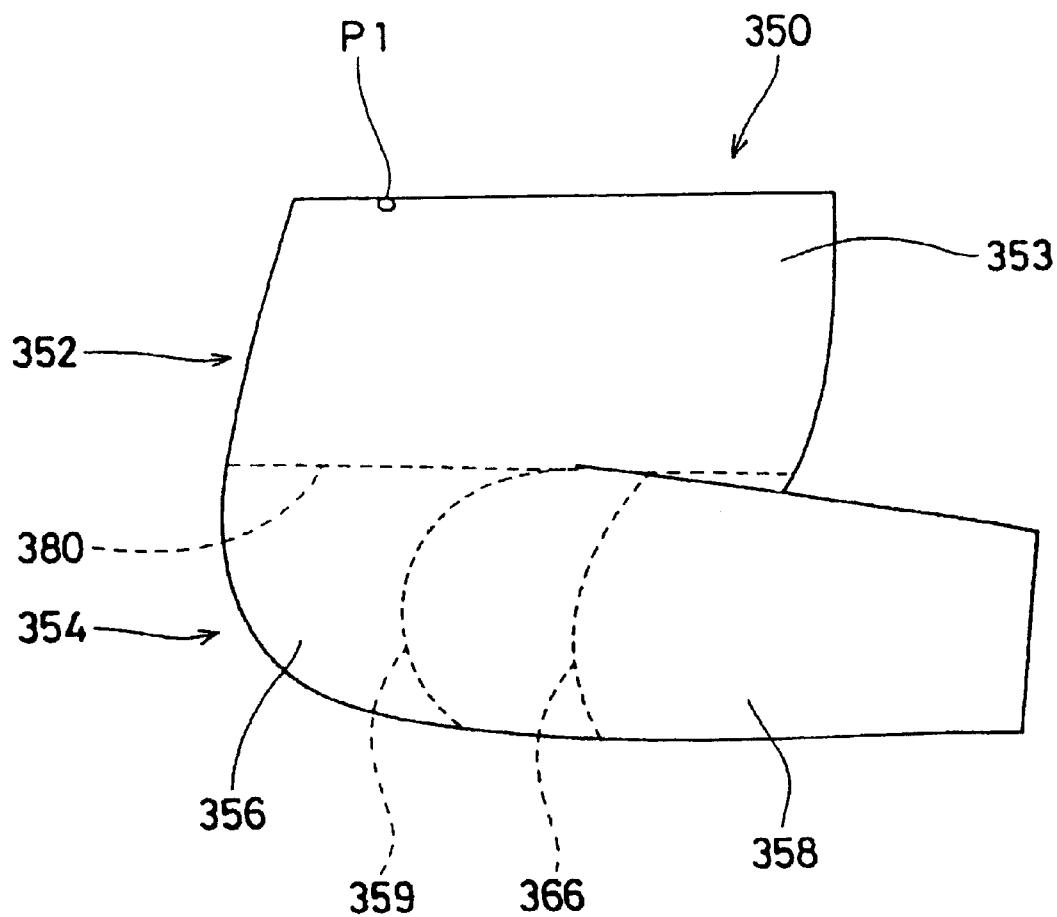
FIG. 18 is a side view of the standard mannequin shown in FIG. 17.
Figure 19:
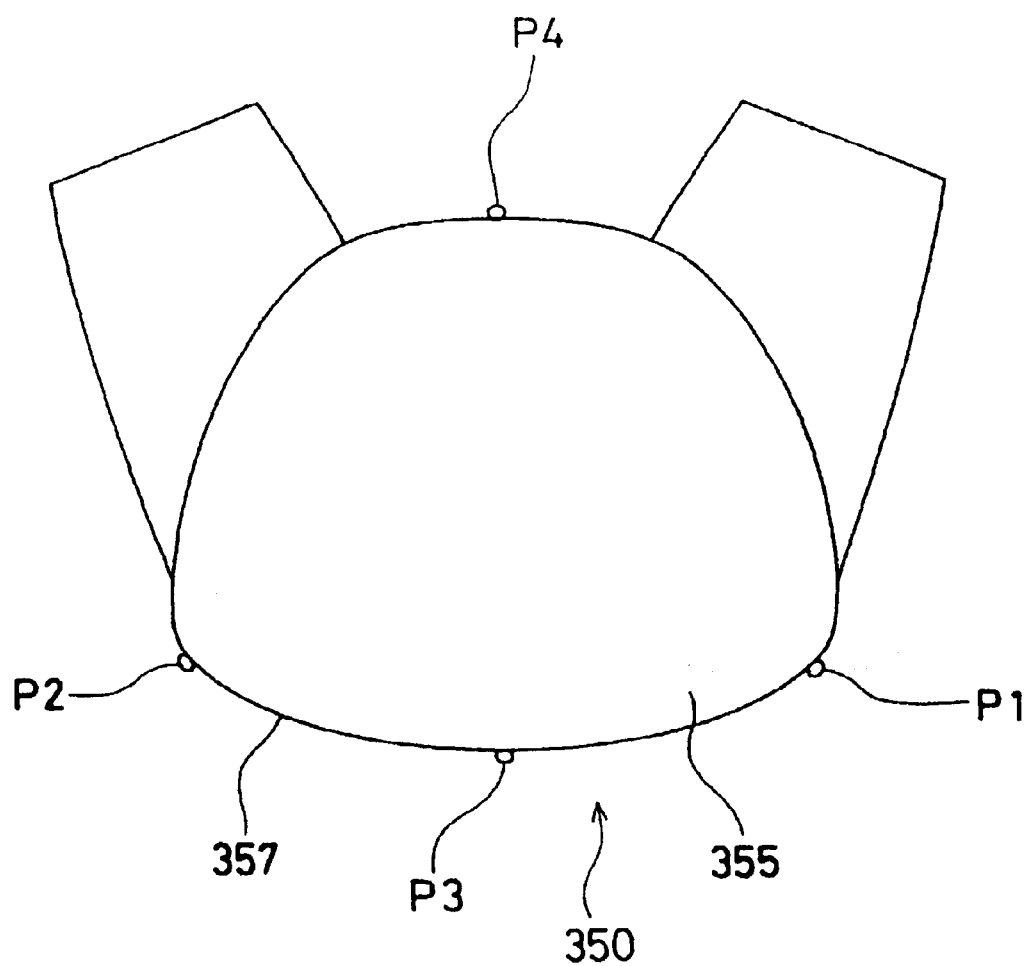
FIG. 19 is a top view of the standard mannequin shown in FIG. 17.

FIG. 15 shows one preferred example of the force versus extension curves of the continuous belt zone 38 of the pull-on diaper. FIG. 16 shows the modulus of extensibility versus extension curve of the example shown in FIG. 15. The methods to obtain a force versus extension curve of the continuous belt zone 38 and a modulus of extensibility versus extension curve are set forth below.

The methods to obtain a force versus extension curve of the continuous belt zone and a modulus of extensibility versus extension curve are set forth below. This method is a modified ultimate tensile test method contained within the "Sintech TestWorks" software package for measuring a force versus extension curve. This measurement is basically designed to simulate the applicator habit in putting a pull-on diaper on the wearer by using the Instron force tester and two horizontal bars in the place of the jaws starting from 0 g force to 10,000 g force or when the diaper breaks, which represents the ultimate force applied to the continuous belt zone. The method gives "force versus extension" curve from the untensioned condition up to the ultimate tensile of the diaper. The force versus extension data generated as described above can then be converted to "modulus of extensibility versus extension".

This test method requires sample preparation as described below.
(1) The sample diaper to be tested should be taken from the bag
(2) Measure the diaper inside circumference at the waist edge of the diaper using measuring tape without stretching diaper during the measurement (Untensioned Diaper Circumference)

This test method involves the following equipment below.

| | |
|---|---|
| (1) Tensile/Cycle Tester | Instron Model 5564 |
| (2) Operation Software | Sintech TestWorks version 3.0 |
| (3) Loadcell | Instron Static Loadcell 100N |
| (4) Jaw | 20 mm diameter × 150 mm length Teflon coated bar mounted horizontally to upper and lower jaws |

This test method is performed with the setting below.
(1) Test Method: Tensile
(2) Travel Speed: 20 inch/minute (3) Gauge Length: distance of the center of the upper bar and the lower bar is calculated as below (Gauge Length)=(Untensioned Diaper Circumference)/2−30 mm (4) # of Cycle: 1 cycle
(5) Break Sensitivity: 75%
(6) Load Limit: 10,000 g
(7) Calculation Input: Untensioned Diaper Circumference, Load Point at 500 g, 1,000 g, 2,000 g, 3,000 g, 4,000 g, 5,000 g, 6,000 g
(8) Calculation Results: Diaper Circumference at 0 g (=untensioned), extension at load point at 500 g, at 1,000 g, at 2,000 g, at 3,000 g, at 4,000 g, at 5,000 g, at 6,000 g, at Peakload, Load at Peak, circumference at peak load Diaper circumference at certain load point is calculated as below (Diaper Circumference)=(Untensioned Diaper Circumference)+(extension)×2

Extension at certain load point is calculated as below.

(Extension)=(Extended Diaper Circumference−Untensioned Diaper Circumference)/(Untensioned Diaper Circumference)

The test method is executed as below.
(1) Prepare sample diapers and measurement data
(2) Set up the Instron Loadcell and Jog following the Instron Setting above then calibrate the Loadcell
(3) Log in to the TestWorks system
(4) Choose tensile test method from the method list tool bar, then let Control Panel, Load Meter, Extension Meter, and Handset show up on the screen
(5) Enter the Untensioned Diaper Circumference data into gauge length in the calculation input
(6) Set up the Gauge Length using a ruler following the Gauge Length Setting described above
  (Example: Untensioned Diaper Circumference=380 mm→Gauge Length=380/2−30=160 mm)
(7) Reset the Load in the Load Meter and Extension in the Extension Meter
(8) Measure the product weight by putting a product to be test on the upper bar then reset the load again
(9) Put the sample diaper on the Jog with checking the cuff/leg elastic does not stick on the bar
(10) After putting the diaper on the jog, do not reset the Load Meter
(11) Click the "Run" to start the measurement
(12) When the measurement has been done, the jog returns to the original position
(13) Click "File" to save the data and remove the diaper
(14) Repeat the step 6–13 for other sample
The data is evaluated as below.
(1) After completion for all samples, export the data into an appropriate spreadsheet program (i.e. Microsoft Excel)
(2) "Force versus extension curve" is obtained by plotting the force in grams against diaper extension in percent
(3) "Modulus of extensibility" is obtained by dividing the force difference between two successive data points by the extension difference between the two same points
(4) "Modulus of extensibility versus extension curve" is obtained by plotting the modulus of extensibility obtained in the step of (3) against diaper extension in percent As stated above, the continuous belt zone 38 creates fit force in the pull-on diaper 20 when positioned on the wearer, to maintain the pull-on diaper 20 on the wearer. The continuous belt zone 38 further includes a zone of extensibility which comprises elastic materials such as the side elastomeric material 124 and the waist elastomeric material 200. The zone of extensibility may further include a leg elastomeric material. The leg elastomeric material comprises elastomeric material such as the elastic strands 64 as shown in FIG. 3. The leg elastomeric material may comprise the material used for the side elastomeric material 124 or the waist elastomeric material 200. Herein "zone of extensibility" refers to a continuous area or a continuous zone of the pull-on diaper rendered extensible by an elastomeric material having the form of a continuous plane layer with or without apertures, or the form of strands which are not connected to each other. The zone of extensibility is that portion in the continuous belt zone 38 which substantially generates the skin contact pressure in the continuous belt zone 38. The skin contact pressure generated by the zone of extensibility contributes to maintaining the pull-on diaper on the wearer (sustained fit of the pull-on diaper). The skin contact pressure in the zone of extensibility may not be uniform everywhere. For example, the skin contact pressure of the zone of extensibility between about the waist opening and about the leg openings may be different from each other. Additionally, the skin contact pressure may vary around the radial circumference of the diaper or the leg circumference of the diaper.

In the zone of extensibility, the elastic component of the elastomeric material (such as a plurality of first strands 125 and a plurality of second strands 127 of the elastomeric scrim 124 shown in FIG. 8) pressing on the skin usually generates higher skin contact pressure than the remainder of the area of the zone of extensibility (such as a plurality of apertures 132 of the elastomeric scrim shown in FIG. 8). Therefore, lower skin contact pressure of the elastomeric material pressing on the skin leads to a reduction of the local skin incidence.

The skin contact pressure of the elastomeric material (side elastomeric material and/or waist elastomeric material) pressing on the skin should be not less than about 0.1 psi to maintain the pull-on diaper 20 on the wearer, preferably not less than about 0.2 psi, more preferably not less than about 0.3 psi. The skin contact pressure of the elastomeric material (side elastomeric material and/or waist elastomeric material) pressing on the skin should be not greater than about 0.75 psi not to cause the skin incidence in the zone of extensibility, preferably not greater than about 0.65 psi, more preferably not greater than about 0.55 psi. Any combination selected from the above range of the skin contact pressure of the elastomeric material pressing on the skin is effective in providing a pull-on diaper with a reduced risk of drooping, sagging or sliding down from the position on the wearer, with a reduced risk of skin incidence in the zone of extensibility, and with a reduced risk of skin incidence by the elastomeric material. The skin contact pressure of the elastomeric material (leg elastomeric material) pressing on the skin should be not less than about 0.1 psi to maintain the pull-on diaper 20 on the wearer, preferably not less than about 0.2 psi, more preferably not less than about 0.3 psi. The skin contact pressure of the elastomeric material (leg elastomeric material) pressing on the skin should be not greater than about 0.75 psi not to cause the skin incidence in the zone of extensibility, preferably not greater than about 0.65 psi, more preferably not greater than about 0.55 psi. The method to obtain the skin contact pressure of the elastomeric material pressing on the skin is set forth below.

The skin contact pressure of the elastomeric material pressing on the skin within the zone of extensibility about the waist opening may be higher than the skin contact pressure of the elastomeric material pressing on the skin at the remainder of the area within the zone of the extensibility to provide a sustained fit of the pull-on diaper about the waist opening. The skin contact pressure of the elastomeric material pressing on the skin within the zone of extensibility about the leg openings may be higher than the skin contact pressure of the elastomeric material pressing on the skin at the remainder of the area of the zone of the extensibility to provide a sustained fit of the pull-on diaper about the leg openings. The skin contact pressure of the elastomeric material pressing on the skin about the waist opening and about the leg openings within the zone of extensibility may be higher than the skin contact pressure of the elastomeric material pressing on the skin at the remainder of the area within the zone of the extensibility. The difference between the highest skin contact pressure of the elastomeric material pressing on the skin within the zone of extensibility and the lowest skin contact pressure of the elastomeric material pressing on the skin should be less than about 0.65 psi, preferably less than about 0.45 psi, more preferably less than about 0.25 psi. As the difference becomes closer to zero, the skin contact pressure of the elastomeric material pressing on the skin within the zone of extensibility becomes closer to uniform everywhere. This further contributes to reduce a skin incidence which have caused by the different pressure.

The pull-on diaper 20 further comprises additional elastomeric material such as the spacing means 58 of the inner barrier cuff 54. It is preferable that these additional elastomeric material incorporated in the pull-on diaper 20 gives skin contact pressure of the additional elastomeric material pressing on the skin of the wearer of not greater than about 0.75 psi. Preferably, the skin contact pressure of the additional elastomeric material pressing on the skin of the wearer is not greater than about 0.65 psi, more preferably not greater than about 0.55 psi.

The method to measure the skin contact pressure of the elastomeric material pressing on the skin within the zone of extensibility is set forth below. The method entitled "AMI Air-pack Type Contact Surface Pressure Measurement System" is commercially supplied by AMI Co., Ltd to measure the surface contacting pressure generated between soft materials. This method is modified to measure the contacting pressure between the diaper and wearer's body. Air pressure indicated represents the force of contact surface from which the force absorbed by ductility of the material has been deducted. The sensing part is composed of an air pack made of a very soft thin film, of a tube introducing to the main unit and the measured value is converted into DC output (10 mV=1 gf/cm$^2$).

This test method requires sample preparation below.
(1) The sample diaper to be tested should be taken from the bag
(2) Measure the width of the actual elastomeric component of the elastomeric material (i.e. elastic strands) under the 50% stretched condition and calculate the percent area of the elastomeric component This test method entitled "AMI Air-pack Type Contact Surface Pressure Measurement System" involves the following equipment below.

| | |
|---|---|
| (1) Air-pack | AMI Co., Ltd Model Ø15 mm |
| (2) Main Unit | AMI Co., Ltd AMI 3037-2 |
| (3) Option Unit | AMI Co., Ltd AMI 3037-2B |
| (4) Air Cylinder | AMI Co., Ltd |
| (5) Calibration Set | AMI Co., Ltd |
| (6) Data Collector | ANRITSU METER Co., Ltd. AM-7052 |

-continued

| | |
|---|---|
| (7) Data Converting Software | ANRITSU METER Co., Ltd. DATA COLLECTOR System AMS7006WIN ver. 2.0 for Windows |

This test equipment described above requires the setting below.
(1) Connect the output cable to the output connector of the main unit and connect the opposite side of the output cable to the data collector
(2) Turn on the power
(3) Use the gear, push the head of air cylinder to the end in the shortest length
(4) Connect the air pack to the air cylinder
(5) Insert the pin into the blue head on the gear, turn the gear until the pin comes to the end, wait 3 seconds
(6) Press the release lever for making air cylinder pressure to be the same with and ambient pressure, wait 3 seconds
(7) Insert the pin into the hole of the gear whose color is the same with the air pack, turn the gear until the pin comes to the end
(8) Remove the air pack from the air cylinder, turn the gear until the pin comes to the end
(9) Check if the output signal from the main unit is close to zero with allowance of 5 mV (0.5 gf/cm$^2$)
(10) Connect the air pack to the main unit (connection should be made in one action. If you renew connection, inside volume of air pack must be change)
(11) Press the air pack by hand flat or finger for removing all the air from the air pack, check the output signal transmitted from the main unit, be careful that this is the maximum measurement value and that the system can't measure any values exceeding the maximum the maximum measurement value. If the contact surface is bent too much, and if output signal from the main unit exceeds +20 mV (2 gf/cm$^2$), connect the air cylinder and press the release lever
(12) Prepare at least 2 air-packs for standard measurement This method requires a standard mannequin as below.

The standard mannequin 350 shown in FIGS. 20 and 21 is modeled after the body shape in a sitting posture of the wearer. The shape and the dimension of the standard mannequin 350 should be based on the body dimension data taken from the actual diaper users. The standard mannequin 350 has an upper portion 352 and a lower portion 354. The upper portion 352 and the lower portion 354 are divided by the lower torso line 380. The lower torso line 380 is the circumferential line through the upper portion of the pubic bone. The upper portion 352 includes a torso portion 353. The torso portion 353 has an upper surface 355 (shown in FIG. 22) surrounded by the waist line 357 which is the circumference line about the top waist of the torso portion 353. The torso portion 353 has a height defined by the height between the waist line 357 and the lower torso line 380. The circumference of the torso portion 353 gradually increases from the waist line 357 toward the lower torso line 380. The lower portion 354 includes a hip portion 356 at the back of the lower portion 354, and the leg portions 358 protruding from the hip portion 356 at the front of the lower portion 354. The hip portion 356 and the leg portions 358 are divided by the crotch crease line 359 along the fat fold at the front of the body. The two leg portions 358 have a crotch angle 362 which is the angle subtended between the inner thighs 364. The leg portion 358 has a thigh line 366 which is the circumferential line about the thigh of the leg portion 358. The upper surface 355 has a shape surrounded by the waist line 357 which comprises straight lines and curve lines. FIG. 22 shows one preferred example of the shape of the upper surface 355 which is determined based on the actual wearer dimension. The standard mannequin is made of vinyl chloride.

The actual dimension of the standard mannequin for a diaper designed to fit the wearer weighing from about 7.0 kgs to about 10.0 kgs is shown below.

| | |
|---|---|
| Circumference at the waist line: | 460 mm |
| Circumference at the lower torso line: | 470 mm |
| Circumference at the crotch crease line: | 310 mm |
| Circumference at the thigh line: | 275 mm |
| Height of the torso: | 75 mm |
| Crotch angle: | about 60 degrees |

The actual dimension of the standard mannequin for a diaper designed to fit the wearer weighing from about 9.0 kgs to about 14.0 kgs is shown below.

| | |
|---|---|
| Circumference at the waist line: | 495 mm |
| Circumference at the lower torso line: | 505 mm |
| Circumference at the crotch crease line: | 330 mm |
| Circumference at the thigh line: | 290 mm |
| Height of the torso: | 80 mm |
| Crotch angle: | about 60 degrees |

The actual dimension of the standard mannequin for a diaper designed to fit the wearer weighing from about 13.0 kgs or above is shown below.

| | |
|---|---|
| Circumference at the waist line: | 520 mm |
| Circumference at the lower torso line; | 530 mm |
| Circumference at the crotch crease line: | 350 mm |
| Circumference at the thigh line: | 305 mm |
| Height of the torso: | 85 mm |
| Crotch angle: | about 60 degrees |

The measurement points for the waist elastomeric material and the side elastomeric material are determined as below.

Point P1 is the point of the minimum radius of the waist curvature line at the right side of the torso portion. Point P2 is the point of the minimum radius of the waist curvature line at the left side of the torso portion. Point P3 is the point at the center of the back of the torso portion. Point P4 is the point at the center of the front of the torso portion. The for the measurement point P1, P2, P3, and P4 should be mounted about 10 mm below the waist line and should be fully covered by the waist material of the sample diaper. Point P5 is the point at the front of the right leg portion and point P6 is the point at the front of the left leg portion. The Air-packs for the measurement point P5 and P6 should be mounted right under the elastomeric material contacting the mannequin's leg portion.

The measurement points for the leg elastomeric material are the points where the elastomeric material presses on the skin of the standard mannequin.

This method is executed as below.
(1) Set up the pressure measurement system following the setting above
(2) Prepare sample diapers and mount the diaper on the standard mannequin
(3) Place two Air-packs at the point P1 and P2 and measure the pressure
(4) Record the pressure measurement data and check if the pressure signal recovers close to zero with allowance of 5 mV (0.5 gf/cm$^2$)
(5) Place two Air-packs at the point P3 and P4 and measure the pressure
(6) Record the pressure measurement data and check if the pressure signal recovers close to zero with allowance of 5 mV (0.5 gf/cm$^2$)
(7) Place two Air-packs at the point P5 and P6 and measure the pressure
(8) Record the pressure measurement data and check if the pressure signal recovers close to zero with allowance of 5 mV (0.5 gf/cm$^2$)
(9) Repeat the step 2 to 8 for 1 sample diaper
The data is evaluated as below.
(1) "Local average skin contact pressure within the zone of extensibility" is obtained by convert the measured voltage into psi (10 mV=1 gm/cm$^2$)
(2) "Skin contact pressure of the elastomeric material pressing on the skin " is then obtained in psi by dividing the "local average skin contact pressure within the zone of extensibility" obtained above by the percent area of the elastomeric component It is understood that the examples and embodiments described herein are for illustrative purpose only and that various modifications or changes will be suggested to one skilled in the art without depending from the scope of the present invention.

What is claimed is:
1. A disposable garment having a front region, a back region and a crotch region between the front region and the back region, the disposable garment comprising:
   a chassis comprising a topsheet, a backsheet joined with the topsheet, and an absorbent core interposed between the topsheet and the backsheet, the chassis having a central panel having side edges and a waist edge, and an ear panel extending laterally outwardly from each side edge of the central panel in the front region and the back region,
   wherein the ear panel is rendered extensible to form an extensible ear, the extensible ear having a higher end edge, a lower end edge, an inner side edge, and an outer side edge defined by a substantially straight line connecting an outer end point of the higher end edge and an outer end point of the lower end edge,
   wherein the outer side edge is non-parallel to the inner side edge, and is non-parallel to a longitudinal center line of the garment, and projects laterally outwardly proximate the higher end edge,
   wherein a lateral width of the extensible ear between the inner side edge and the outer side edge is greater proximate the higher end edge than proximate the lower end edge, and
   seams joining each ear panel along the outer side edge to a corresponding portion in the opposite region of the disposable garment so as to form one waist and two leg openings,
   wherein the seam is non-parallel to the longitudinal center line.
2. The disposable garment of claim 1 wherein the ear panel has a waist edge, wherein the chassis has a waistband panel extending longitudinally outwardly from each waist edge of the central panel and the waist edge of the ear panel in the front region and the back region, wherein the waistband panel is rendered extensible to form an extensible waistband.
3. The disposable garment of claim 1 wherein the extensible ear comprises a side elastomeric material.

4. The disposable garment of claim 2 wherein the extensible waistband comprises a waist elastomeric material.

5. The disposable garment of claim 1 wherein the extensible ear comprises a side elastomeric material and the extensible waistband comprises a waist elastomeric material, wherein the waist elastomeric material and the side elastomeric material are separate elements and disposed so as not to overlap each other.

6. The disposable garment of claim 4 wherein the waistband panel has an original length before the waist elastomeric material is joined thereto, wherein the extensible waistband is rendered extensible such that the extensible waistband extends beyond the original length of the waistband panel.

7. The disposable garment of claim 6 wherein at least a part of the waist elastomeric material is prestrained before joined to the waistband panel.

8. The disposable garment of claim 3 wherein the extensible ear is formed from a "zero strain" stretch laminate.

9. The disposable garment of claim 3 wherein the side elastomeric material is in the form of a continuous plane layer.

10. The disposable garment of claim 3 wherein the side elastomeric material is in the form of strands which are not connected each other.

* * * * *